(12) United States Patent
Kurek et al.

(10) Patent No.: US 8,546,648 B2
(45) Date of Patent: Oct. 1, 2013

(54) RUBISCO ACTIVASE WITH INCREASED THERMOSTABILITY AND METHODS OF USE THEREOF

(71) Applicant: Pioneer Hi-Bred International, Inc., Johnston, IA (US)

(72) Inventors: Itzhak Kurek, San Francisco, CA (US); Lu Liu, Palo Alto, CA (US); Genhai Zhu, San Jose, CA (US)

(73) Assignee: Pioneer Hi Bred International Inc, Johnston, IA (US)

( * ) Notice: Subject to any disclaimer, the term of this patent is extended or adjusted under 35 U.S.C. 154(b) by 0 days.

(21) Appl. No.: 13/621,895

(22) Filed: Sep. 18, 2012

(65) Prior Publication Data
US 2013/0019344 A1 Jan. 17, 2013

Related U.S. Application Data

(62) Division of application No. 12/723,779, filed on Mar. 15, 2010, which is a division of application No. 12/474,298, filed on May 29, 2009, now Pat. No. 7,723,573, which is a division of application No. 11/867,723, filed on Oct. 5, 2007, now Pat. No. 7,557,267, which is a division of application No. 11/507,729, filed on Aug. 22, 2006, now Pat. No. 7,314,975.

(60) Provisional application No. 60/711,449, filed on Aug. 24, 2005, provisional application No. 60/733,110, filed on Nov. 2, 2005.

(51) Int. Cl.
*A01H 1/00* (2006.01)
*C12N 15/00* (2006.01)
*C07H 21/04* (2006.01)
*C07K 14/415* (2006.01)
*C12N 15/29* (2006.01)
*C12N 15/52* (2006.01)
*C12N 15/63* (2006.01)

(52) U.S. Cl.
USPC .......... 800/295; 435/6.18; 435/468; 435/183; 435/419; 435/320.1; 530/370; 536/23.2; 536/23.6; 800/278

(58) Field of Classification Search
USPC .............. 435/6.1, 69.1, 468, 183, 419, 320.1; 530/370; 536/23.2, 23.6; 800/278, 295
See application file for complete search history.

(56) References Cited

FOREIGN PATENT DOCUMENTS

EP 1033405 A2 9/2000

OTHER PUBLICATIONS

Kallis, et al.; "Alteration of the Adenine Nucleotide Response and Increased Rubisco Activity of *Arabidopsis* Rubisco Activae by Site-Directed Mutagenesis"; Plant Physiology (Jul. 2000) 123(3):1077-1086; American Society of Plant Physiologists; Rockville, MD US.
Alexandrov, et al.; A_Geneseq Acc. No. AAG31720; EP1033405-A2, Sep. 6, 2000; Result 12.

*Primary Examiner* — Phuong Bui
(74) *Attorney, Agent, or Firm* — Pioneer Hi-Bred Int'l Inc.

(57) ABSTRACT

The present invention provides thermostable polypeptides related to *Arabidopsis* Rubisco Activase polypeptides. Nucleic acids encoding the polypeptides of the invention are also provided. Methods for using the polypeptides and nuclei acids of the invention to enhance resistance of plants to heat stress are encompassed.

3 Claims, 6 Drawing Sheets

RUBISCO ACTIVASE WITH INCREASED THERMOSTABILITY AND METHODS OF USE THEREOF

CROSS-REFERENCE TO RELATED APPLICATION

This utility application is a divisional application claiming benefit from U.S. Utility patent application Ser. No. 12/723,779 filed Mar. 15, 2010, now abandoned, which is a divisional of U.S. Utility patent application Ser. No. 12/474,298 filed May 29, 2009, now granted U.S. Pat. No. 7,723,573 issued May 25, 2010, which is a divisional of U.S. Utility patent application Ser. No. 11/867,723, filed Oct. 5, 2007, now granted U.S. Pat. No. 7,557,267 issued Jul. 7, 2009, which is a divisional of U.S. Utility patent application Ser. No. 11/507,729, filed Aug. 22, 2006, now granted U.S. Pat. No. 7,314,975 issued Jan. 1, 2008, which also claims the benefit U.S. Provisional Patent Application Ser. No. 60/711,449, filed Aug. 24, 2005 and U.S. Provisional Serial Application No. 60/733,110, filed Nov. 2, 2005, all of which are incorporated herein by reference.

FIELD OF THE INVENTION

The present invention relates generally to increasing the levels of photosynthesis in plants grown under increased temperatures. More particularly, the present invention relates to improving the thermostability of the photosynthetic enzyme Rubisco Activase.

BACKGROUND OF THE INVENTION

Ribulose-1,5-bisphosphate carboxylase/oxygenase (Rubisco) is an important enzyme in the photosynthetic process. This enzyme incorporates $CO_2$ into plants during photosynthesis. Atmospheric oxygen competes with $CO_2$ as a substrate for Rubisco, giving rise to photorespiration and making Rubisco the rate-limiting step in photosynthesis.

Rubisco Activase (RCA) is a protein that catalyzes the activation of Rubisco, which in turn, regulates photosynthesis by initiating photosynthetic carbon reduction and photorespiratory carbon oxidation. The Rubisco Activase enzyme catalyzes the release of ribulose-1,5-bisphosphate (RuBP) from Rubisco. This newly unoccupied site on Rubisco is now free to bind the $CO_2$ and $Mg^{2+}$ activators in order for photosynthesis to proceed. Rubisco Activase is also responsible for releasing sugar phosphate inhibitors from Rubisco and restores Rubisco catalytic activity. Thus, if Rubisco Activase is impaired, Rubisco remains inactive and photosynthesis slows.

Rubisco Activase is thermo-labile and thus has decreasing activity with increasing temperatures. As a result, the photosynthetic process slows due to the lack of Rubisco activation. The Rubisco Activase enzyme denatures under increased temperatures, thus rendering the enzyme unable to convert inactive Rubisco to the active form. *Arabidopsis* contains two RCA isoforms, the short thermolabile (RCA1) and the long relatively thermostable (RCA2) forms that are generated by alternative splicing of pre-mRNA (Werneke, et al., (1989) *Plant Cell* 1:815-825).

Crop plants grown in hot climates could benefit from increasing photosynthetic levels. Accordingly, if the rate limiting step in photosynthesis could be made more heat tolerant, crop plants could more easily grow in these climates.

SUMMARY OF THE INVENTION

The present invention relates to Rubisco Activase derived polypeptides that are more thermostable than naturally occurring Rubisco Activase. The Rubisco Activase derived polypeptides of the invention substantially retain activity in plants grown under conditions of increased temperature. Nucleic acid molecules encoding the polypeptides of the invention are also encompassed.

In addition to the Rubisco Activase derived polypeptides of the invention, it will be appreciated that the invention also encompasses variants thereof, including, but not limited to, any substantially similar sequence, any fragment, analog, homolog, mutant or modified polypeptide thereof. The variants encompassed by the invention are at least partially functionally active (i.e., they are capable of displaying one or more known functional activities associated with wild type Rubisco Activase) under heated conditions. Nucleic acid molecules encoding the variant polypeptides are also encompassed.

Vectors comprising one or more nucleic acids of the invention are also encompassed.

Cells comprising a polypeptide, nucleic acid molecule and/or vector of the invention are also encompassed.

The present invention also relates to transgenic plants comprising a polypeptide, nucleic acid molecule, and/or vector of the invention. The transgenic plants can express the transgene in any way known in the art including, but not limited to, constitutive expression, developmentally regulated expression, tissue specific expression, etc. Seed obtained from a transgenic plant of the invention is also encompassed.

DETAILED DESCRIPTION

Figure 1:
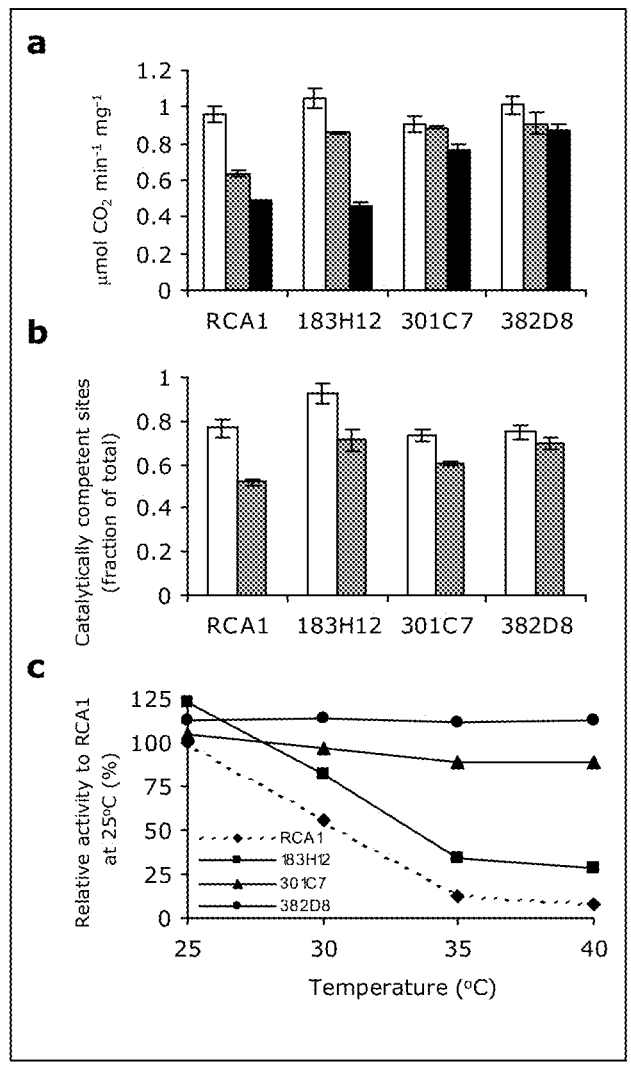
FIGS. 1A-1C: Characterization of wild type RCA (RCA1) and thermostable variants (183H12, 301C7 and 382D8). (A) Rubisco activity after activation by activase after treatment at 25° C. (white), 40° C. (gray) and 45° C. (black). Activase proteins were incubated at the indicated temperatures for 15 min prior to assay at 25° C. (B) Activation of Rubisco under catalytic conditions at 25° C. (white) and 40° C. (gray). (C) ATPase activity of activase proteins incubated at the indicated temperatures for 15 min prior to assay at 25° C.

The present invention provides polypeptides derived from Rubisco Activase. Nucleic acid molecules encoding the polypeptides of the invention are also provided. Methods for using the polypeptides and nucleic acids of the invention to increase the heat-tolerance of plants comprising enhancing the thermostability of Rubisco Activase are encompassed.

Polypeptides of the Invention

The present invention relates to Rubisco Activase derived polypeptides that are more thermostable than naturally occurring Rubisco Activase. In preferred embodiments, the Rubisco Activase derived polypeptide is any of SEQ ID NOS: 4, 6, 8, 10, 12, 14, 16, 18, 20 and 22. Polypeptides of the invention also encompass those polypeptides that are encoded by any Rubisco Activase derived nucleic acid of the invention.

In addition to the Rubisco Activase derived polypeptides of the invention, it will be appreciated that the invention also encompasses variants thereof, including, but not limited to, any substantially similar sequence, any fusion polypeptide, any fragment, analog, homolog, mutant or modified polypeptide thereof. The variants encompassed by the invention are at least partially functionally active (i.e., they are capable of displaying one or more known functional activities associated with wild type Rubisco Activase) under heated conditions. Such functional activities include, but are not limited to, biological activities, such as activation of Rubisco; antigenicity, i.e., an ability to bind or compete with wild type Rubisco Activase (including, but not limited to, SEQ ID NO: 2) for binding to an anti-Rubisco Activase antibody; immunogenicity, i.e., an ability to generate antibody which binds to a wild type Rubisco Activase polypeptide. In preferred embodiments, the variants have at least one functional activity that is substantially similar to or better than its parent polypeptide (i.e., the unaltered Rubisco Activase derived polypeptide). As used herein, the functional activity of the variant will be considered "substantially similar" to its parent polypeptide if it is within one standard deviation of the parent.

In one embodiment, polypeptides that have at least one functional activity of Rubisco Activase (e.g., Rubisco activation) under heated conditions and are at least 85%, 90%, 95%, 97%, 98% or 99% identical to the polypeptide sequence of any of SEQ ID NOS: 4, 6, 8, 10, 12, 14, 16, 18, 20 and 22 are encompassed by the invention. In specific embodiments, such polypeptides of the invention are altered at one or more, two or more, five or more, or seven or more positions corresponding to residues 42, 130, 131, 168, 257, 274, 293 and 310 of SEQ ID NO: 2 upon optimal alignment of the polypeptide sequence with SEQ ID NO: 2. With respect to an amino acid sequence that is optimally aligned with a reference sequence, an amino acid "corresponds" to the position in the reference sequence with which the residue is paired in the alignment.

As used herein, where a sequence is defined as being "at least X % identical" to a reference sequence, e.g., "a polypeptide at least 95% identical to SEQ ID NO: 4," it is to be understood that "X % identical" refers to absolute percent identity, unless otherwise indicated. The term "absolute percent identity" refers to a percentage of sequence identity determined by scoring identical amino acids or nucleic acids as one and any substitution as zero, regardless of the similarity of mismatched amino acids or nucleic acids. In a typical sequence alignment the "absolute percent identity" of two sequences is presented as a percentage of amino acid or nucleic acid "identities." In cases where an optimal alignment of two sequences requires the insertion of a gap in one or both of the sequences, an amino acid residue in one sequence that aligns with a gap in the other sequence is counted as a mismatch for purposes of determining percent identity. Gaps can be internal or external, i.e., a truncation. Absolute percent identity can be readily determined using, for example, the Clustal W program, version 1.8, June 1999, using default parameters (Thompson, et al., (1994) *Nucleic Acids Research* 22:4673-4680).

In another embodiment, fusion polypeptides comprising a Rubisco Activase derived polypeptide or variant thereof are encompassed by the invention. In a specific embodiment, a peptide (such as those disclosed in U.S. patent application Ser. No. 11/150,054) is added onto a polypeptide of the invention, whereby the peptide directs localization of the attached polypeptide to the plant plastids or the plant photosynthetic organs.

In another embodiment, fragments of Rubisco Activase derived polypeptides are encompassed by the invention. Polypeptides are encompassed that have at least one functional activity (e.g., Rubisco activation) of Rubisco Activase under heated conditions and are at least 25, 50, 75, 100, 125, 150, 175, 200, 225, 250, 275, 300, 325, 350, 375 or 380 contiguous amino acids in length of any of SEQ ID NOS: 4, 6, 8, 10, 12, 14, 16, 18, 20 and 22. In preferred embodiments, the polynucleotide that encodes the fragment polypeptide hybridizes under stringent conditions to the nucleic acid that encodes any of SEQ ID NOS: 4, 6, 8, 10, 12, 14, 16, 18, 20 and 22.

In a specific embodiment, a fragment of the invention corresponds to a functional domain of Rubisco Activase including, but not limited to, the ATP binding domain and the substrate interaction domain (see, e.g., Li, et al., (2005) *J Biol Chem* 280:24864-24869; Salvucci, et al., (1994) *Biochemistry* 33:14879-14886 and van de Loo, et al., (1996) *Biochemistry* 35:8143-8148).

In another embodiment, analog polypeptides are encompassed by the invention. Analog polypeptides may possess residues that have been modified, i.e., by the covalent attachment of any type of molecule to the Rubisco Activase derived polypeptides. For example, but not by way of limitation, an analog polypeptide of the invention may be modified, e.g., by glycosylation, acetylation, pegylation, phosphorylation, amidation, derivatization by known protecting/blocking groups, proteolytic cleavage, linkage to a cellular ligand or other protein, etc. An analog polypeptide of the invention may be modified by chemical modifications using techniques known to those of skill in the art, including, but not limited to specific chemical cleavage, acetylation, formylation, metabolic synthesis of tunicamycin, etc. Furthermore, an analog of a polypeptide of the invention may contain one or more non-classical amino acids.

In another embodiment of the invention, a Rubisco Activase derived polypeptide is not SEQ ID NO: 2. In yet another embodiment of the invention, a Rubisco Activase derived polypeptide is not a naturally occurring wild type polypeptide.

Methods of production of the polypeptides of the invention, e.g., by recombinant means, are also provided.

Nucleic Acid Molecules of the Invention

The present invention also relates to the nucleic acid molecules encoding Rubisco Activase derived polypeptides. In preferred embodiments, the Rubisco Activase derived nucleic acid molecule is any of SEQ ID NOS: 3, 5, 7, 9, 11, 13, 15, 17, 19 and 21. Nucleic acid molecules of the invention also encompass those nucleic acid molecules that encode any Rubisco Activase derived polypeptides of the invention.

In addition to the nucleic acid molecules encoding Rubisco Activase derived polypeptides, it will be appreciated that nucleic acid molecules of the invention also encompass those encoding polypeptides that are variants of Rubisco Activase derived polypeptides, including, but not limited to any substantially similar sequence, any fusion polypeptide, any fragment, analog, homolog, mutant or modified polypeptide thereof. The nucleic acid molecule variants encompassed by the invention encode polypeptides that are at least partially functionally active (i.e., they are capable of displaying one or more known functional activities associated with wild type Rubisco Activase) under heated conditions.

In one embodiment, nucleic acid molecules that are at least 70%, 75%, 80%, 85%, 90%, 95%, 97%, 98% or 99% identical to any of the nucleic acid molecules of SEQ ID NOS: 3, 5, 7, 9, 11, 13, 15, 17, 19 and 21 are encompassed by the invention. In specific embodiments, such nucleic acid molecules of the invention encode polypeptides that are altered at one or more, two or more, five or more, or seven or more positions corresponding to residues 42, 130, 131, 168, 257, 274, 293 and 310 of SEQ ID NO: 2 upon optimal alignment of the nucleotide sequence with SEQ ID NO: 2.

To determine the percent identity of two nucleic acid molecules, the sequences are aligned for optimal comparison purposes (e.g., gaps can be introduced in the sequence of a first nucleic acid molecule for optimal alignment with a second or nucleic acid molecule). The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences (i.e., % identity=number of identical overlapping positions/total number of positions×100%). In one embodiment, the two sequences are the same length.

The determination of percent identity between two sequences can also be accomplished using a mathematical algorithm. A non-limiting example of a mathematical algorithm utilized for the comparison of two sequences is the algorithm of Karlin and Altschul (Karlin and Altschul, (1990) *Proc. Natl. Acad. Sci.* 87:2264-2268, modified as in Karlin and Altschul, (1993) *Proc. Natl. Acad. Sci.* 90:5873-5877). Such an algorithm is incorporated into the NBLAST and XBLAST programs (Altschul, et al., (1990) *J. Mol. Biol.* 215:403 and Altschul, et al., (1997) *Nucleic Acid Res.* 25:3389-3402). Software for performing BLAST analyses is publicly available, e.g., through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul, et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For polypeptides, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a wordlength (W) of 11, an expectation (E) of 10, a cutoff of 100, M=5, N=−4 and a comparison of both strands. For polypeptides, the BLASTP program uses as defaults a wordlength (W) of 3, an expectation (E) of 10 and the BLOSUM62 scoring matrix (see, Henikoff and Henikoff, (1989) *PNAS* 89:10915).

The Clustal V method of alignment can also be used to determine percent identity (Higgins and Sharp, (1989) *CABIOS* 5:151-153) and found in the Megalign program of the LASERGENE bioinformatics computing suite (DNASTAR Inc., Madison, Wis.). The "default parameters" are the parameters pre-set by the manufacturer of the program and for multiple alignments they correspond to GAP PENALTY=10 and GAP LENGTH PENALTY=10, while for pairwise alignments they are KTUPLE 1, GAP PENALTY=3, WINDOW=5 and DIAGONALS SAVED=5. After alignment of the sequences, using the Clustal V program, it is possible to obtain a "percent identity" by viewing the "sequence distances" table on the same program.

The percent identity between two sequences can be determined using techniques similar to those described above, with or without allowing gaps. In calculating percent identity, typically only exact matches are counted.

In another embodiment, fragments of Rubisco Activase derived nucleic acid molecules are encompassed by the invention. Nucleic acid molecules are encompassed that have at least one functional activity of Rubisco Activase (e.g., Rubisco activation) under heated conditions and are at least 100, 250, 500, 750, 950, 1000 or 1100 contiguous nucleotides in length of any of SEQ ID NOS: 3, 5, 7, 9, 11, 13, 15, 17, 19 and 21.

In a specific embodiment, a fragment of the invention corresponds to a nucleic acid molecule that encodes a functional domain of Rubisco Activase including, but not limited to, the ATP binding domain and the substrate interaction domain (see, e.g., Li, et al., (2005) *J Biol Chem* 280:24864-24869; Salvucci, et al., (1994) *Biochemistry* 33:14879-14886 and van de Loo, et al., (1996) *Biochemistry* 35:8143-8148).

In another embodiment, a nucleic acid molecule that hybridizes under stringent conditions to any one of SEQ ID NOS: 3, 5, 7, 9, 11, 13, 15, 17, 19 and 21 is encompassed by the invention. The phrase "stringent conditions" refers to hybridization conditions under which a nucleic acid will hybridize to its target nucleic acid, typically in a complex mixture of nucleic acid, but to essentially no other nucleic acids. Stringent conditions are sequence-dependent and will be different in different circumstances. Longer nucleic acids hybridize specifically at higher temperatures. Extensive guides to the hybridization of nucleic acids can be found in the art (e.g., Tijssen, *Techniques in Biochemistry and Molecular Biology—Hybridization with Nucleic Probes*, "Overview of principles of hybridization and the strategy of nucleic acid assays" (1993)). Generally, highly stringent conditions are selected to be about 5-10° C. lower than the thermal melting point ($T_m$) for the specific nucleic acid at a defined ionic strength pH. Low stringency conditions are generally selected to be about 15-30° C. below the $T_m$. The $T_m$ is the temperature (under defined ionic strength, pH, and nucleic acid concentration) at which 50% of the probes complementary to the target hybridize to the target nucleic acid at equilibrium (as the target nucleic acids are present in excess, at $T_m$, 50% of the probes are occupied at equilibrium). Hybridization conditions are typically those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, and preferably 10 times background hybridization. The phrase "specifically hybridizes" refers to the binding, duplexing, or hybridizing of a molecule only to a particular nucleotide sequence under stringent hybridization conditions when that sequence is present in a complex mixture (e.g., total cellular or library DNA or RNA).

In another embodiment of the invention, a Rubisco Activase derived nucleic acid molecule is not SEQ ID NO: 1. In yet another embodiment of the invention, a Rubisco Activase derived nucleic acid molecule is not a naturally occurring wild type nucleic acid molecule.

Vectors comprising nucleic acid molecules of the invention are also encompassed. Cells or plants comprising the vectors of the invention are also encompassed.

The term "nucleic acid molecule" herein refers to a single or double-stranded polymer of deoxyribonucleotide or ribonucleotide bases read from the 5' to the 3' end. It includes chromosomal DNA, self-replicating plasmids and DNA or RNA that performs a primarily structural role.

Rubisco Activase-Derived Sequences

Rubisco Activase derived polypeptides and nucleic acid molecules of the invention can be created by introducing one or more residue substitutions, additions and/or deletions into a wild type (wt) Rubisco Activase (including, but not limited to, *Arabidopsis* Rubisco Activase (SEQ ID NO: 2)). Generally, Rubisco Activase derived polypeptides are created in order to accentuate a desirable characteristic or reduce an undesirable characteristic of a wild type Rubisco Activase polypeptide. In one embodiment, Rubisco Activase derived polypeptides have improved thermostability over wild type Rubisco Activase. In another embodiment, Rubisco Activase derived polypeptides have enzymatic activity under heated conditions (e.g., 40° C.) that is similar to or higher than the enzyme activity of wild type Rubisco Activase under normal conditions (e.g., 25° C.).

In one embodiment, a wild type Rubisco Activase nucleic acid molecule (e.g., SEQ ID NO: 1) is used as a template to create Rubisco Activase derived nucleic acid molecules. In some embodiments, nucleic acid residues that encode one or more amino acid residues corresponding to residues 42, 130, 131, 168, 257, 274, 293 and 310 of SEQ ID NO: 2 upon optimal alignment of the nucleotide sequence with SEQ ID NO: 2 are altered such that the encoded amino acid is altered.

Sequence alterations can be introduced by standard techniques such as directed molecular evolution techniques e.g., DNA shuffling methods (see, e.g., Christians, et al., (1999) *Nature Biotechnology* 17:259-264; Crameri, et al., (1998) *Nature* 391:288-291; Crameri, et al., (1997) *Nature Biotechnology* 15:436-438; Crameri, et al., (1996) *Nature Biotechnology* 14:315-319; Stemmer, (1994) *Nature* 370:389-391; Stemmer, et al., (1994) *Proc. Natl. Acad. Sci.* 91:10747-10751; U.S. Pat. Nos. 5,605,793; 6,117,679; 6,132,970; 5,939,250; 5,965,408; 6,171,820; International Publication Numbers WO 1995/22625; WO 1997/0078; WO 1997/35966; WO 1998/27230; WO 2000/42651 and WO 2001/75767); site directed mutagenesis (see, e.g., Kunkel, (1985) *Proc. Natl. Acad. Sci.* 82:488-492; Oliphant, et al., (1986) *Gene* 44:177-183); oligonucleotide-directed mutagenesis (see, e.g., Reidhaar-Olson, et al., (1988) *Science* 241:53-57); chemical mutagenesis (see, e.g., Eckert, et al., (1987) *Mutat. Res.* 178:1-10); error prone PCR (see, e.g., Caldwell and Joyce, (1992) *PCR Methods Applic.* 2:28-33) and cassette mutagenesis (see, e.g., Arkin, et al., (1992) Proc. Natl. Acad. Sci., 89:7871-7815); (see generally, e.g., Arnold, (1993) *Curr. Opinion Biotechnol.* 4:450-455; Ling, et al., (1997) *Anal. Biochem.* 254(2):157-78; Dale, et al., (1996) *Methods Mol. Biol.* 57:369-74; Smith, (1985) *Ann. Rev. Genet.* 19:423-462; Botstein, et al., (1985) *Science* 229:1193-1201; Carter, (1986) *Biochem. J.* 237:1-7; Kramer, et al., (1984) *Cell* 38:879-887; Wells, et al., (1985) Gene 34:315-323; Minshull, et al., (1999) *Current Opinion in Chemical Biology* 3:284-290).

In one embodiment, DNA shuffling is used to create Rubisco Activase derived nucleic acid molecules. DNA shuffling can be accomplished in vitro, in vivo, in silico or a combination thereof. In silico methods of recombination can be affected in which genetic algorithms are used in a computer to recombine sequence strings which correspond to homologous (or even non-homologous) nucleic acids. The resulting recombined sequence strings are optionally converted into nucleic acids by synthesis of nucleic acids which correspond to the recombined sequences, e.g., in concert with oligonucleotide synthesis gene reassembly techniques. This approach can generate random, partially random or designed alterations. Many details regarding in silico recombination, including the use of genetic algorithms, genetic operators and the like in computer systems, combined with generation of corresponding nucleic acids as well as combinations of designed nucleic acids (e.g., based on cross-over site selection) as well as designed, pseudo-random or random recombination methods are described in the art (see, e.g., International Publication Numbers WO 2000/42560 and WO 2000/42559).

In another embodiment, targeted mutagenesis is used to create Rubisco Activase derived nucleic acid molecules by choosing particular nucleotide sequences or positions of the wild type Rubisco Activase for alteration. Such targeted mutations can be introduced at any position in the nucleic acid and can be conservative or non-conservative.

A "non-conservative amino acid substitution" is one in which the amino acid residue is replaced with an amino acid residue having a dissimilar side chain. Families of amino acid residues having similar side chains have been defined in the art. These families include amino acids with basic side chains (e.g., lysine, arginine, histidine), acidic side chains (e.g., aspartic acid, glutamic acid, asparagine, glutamine), uncharged polar side chains (e.g., glycine, serine, threonine, tyrosine, cysteine), nonpolar side chains (e.g., alanine, valine, leucine, isoleucine, proline, phenylalanine, methionine, tryptophan), β-branched side chains (e.g., threonine, valine, isoleucine) and aromatic side chains (e.g., tyrosine, phenylalanine, tryptophan, histidine).

Alternatively or in addition to non-conservative amino acid residue substitutions, such targeted mutations can be conservative. A "conservative amino acid substitution" is one in which the amino acid residue is replaced with an amino acid residue having a similar side chain. Following mutagenesis, the encoded protein can be expressed recombinantly and the activity of the protein can be determined.

In some embodiments, substitutions can be made such that the amino acid at position 42 has an uncharged polar side chain or a β-branched side chain, at position 130 has a basic side chain, at position 131 has a nonpolar side chain or a β-branched side chain, at position 168 has a basic side chain, at position 257 has a nonpolar side chain or a β-branched side chain, at position 274 has a basic side chain, at position 293 has a basic side chain and/or at position 310 has an acidic side chain. The amino acid positions can be determined by optimally aligning the amino acid sequence of the encoded Rubisco Activase derived polypeptide with SEQ ID NO: 2.

In another embodiment, random mutagenesis is used to create Rubisco Activase derived nucleic acid molecules. Mutations can be introduced randomly along all or part of the coding sequence (e.g., by saturation mutagenesis). In certain embodiments, nucleotide sequences encoding other related polypeptides that have similar domains, structural motifs, active sites, or that align with a portion of wild type Rubisco Activase with mismatches or imperfect matches, can be used in the mutagenesis process to generate diversity of sequences.

It should be understood that for each mutagenesis step in some of the techniques mentioned above, a number of iterative cycles of any or all of the steps may be performed to optimize the diversity of sequences. The above-described methods can be used in combination in any desired order. In many instances, the methods result in a pool of altered nucleic acid sequences or a pool of recombinant host cells comprising altered nucleic acid sequences. The altered nucleic acid sequences or host cells expressing an altered nucleic acid sequence with the desired characteristics can be identified by screening with one or more assays known in the art. The assays may be carried out under conditions that select for polypeptides possessing the desired physical or chemical characteristics. The alterations in the nucleic acid sequence can be determined by sequencing the nucleic acid molecule encoding the altered polypeptide in the clones.

Additionally, Rubisco Activase derived nucleic acid molecules can be codon optimized, either wholly or in part. Because any one amino acid (except for methionine) is encoded by a number of codons (Table 1), the sequence of the nucleic acid molecule may be changed without changing the encoded amino acid. Codon optimization is when one or more codons are altered at the nucleic acid level to coincide with or better approximate the codon usage of a particular host. The frequency of preferred codon usage exhibited by a host cell can be calculated by averaging frequency of preferred codon usage in a large number of genes expressed by the host cell. This analysis may be limited to genes that are highly expressed by the host cell. U.S. Pat. No. 5,824,864, for example, provides the frequency of codon usage by highly expressed genes exhibited by dicotyledonous plants and monocotyledonous plants. Those having ordinary skill in the art will recognize that tables and other references providing preference information for a wide range of organisms are available in the art.

Methods of Assaying Rubisco Activase Activity

The present invention is directed to Rubisco Activase derived polypeptides with improved thermostability as compared to wild type Rubisco Activase. As used herein, the term "improved thermostability" refers to the increased ability of Rubisco Activase to activate Rubisco under heated conditions as compared to wild type Rubisco Activase. In one embodiment, Rubisco Activase derived polypeptides have enzymatic activity under heated conditions (e.g., 35° C. or higher) that is greater than the enzymatic activity of wild type Rubisco Activase under heated conditions. In another embodiment, Rubisco Activase derived polypeptides have enzymatic activity under heated conditions (e.g., 26° C. or higher, more preferably 40° C. for in vitro assays) that is substantially similar to or higher than the enzyme activity of wild type Rubisco Activase under normal conditions (e.g., 20-25° C., more preferably 25° C. for in vitro assays and 22° C. for in vivo assays). As used herein, the term "substantially similar" refers to enzymatic activity of a Rubisco Activase derived polypeptide that is within one standard deviation of that of wild type Rubisco.

Any method known in the art can be used to assay the activity of Rubisco Activase derived polypeptides (including, but not limited to, Rubisco activation and ATP hydrolysis) under heated conditions.

In some embodiments, Rubisco Activase derived polypeptide activity is assayed in vitro. In one embodiment, Rubisco Activase derived polypeptides can be assayed for their ability to activate Rubisco when incubated in a solution comprising deactivated Rubisco, RuBP, ATP and a source of labeled carbon (e.g., $[C^{14}]NaHCO_3$). Incorporation of labeled carbon into 3-phosphoglyceric acid (GPA) can be monitored as an indication of Rubisco activation. In another embodiment, Rubisco Activase derived polypeptides can be assayed for their ability to hydrolyze ATP when incubated in a solution comprising ATP. The assays can be conducted under heated conditions or under normal conditions after the Rubisco Activase derived polypeptides are heat treated prior to performance of the assay. Purified components can be used as well as cells comprising the components for Rubisco activation.

In other embodiments, Rubisco Activase derived polypeptide activity is assayed in vivo. Plants which do not express wild type Rubisco Activase (e.g., deletion mutants) are made to express one or more Rubisco Activase derived polypeptides and can be analyzed for photosynthesis rates, biomass, growth rates and seed yield under heated growing conditions. The plants may be grown entirely under heated conditions or for shorter periods of time under heated conditions. In one embodiment, photosynthesis rates are measured by analyzing the plants for $CO_2$ fixation. In another embodiment, growth rates are measured by analyzing leaf area of the plants. In another embodiment, seed yield is analyzed by determining seed weight from mature dried plants. In another embodiment, seed yield is analyzed by determining the seed germination rate.

Methods of Enhancing Heat Tolerance in Plants

Rubisco Activase activates Rubisco in plants. Activated Rubisco is involved in photosynthesis and is the rate limiting step of the photosynthetic process. With decreased Rubisco Activase activity, Rubisco remains inactive and photosynthesis slows or stops. Increased temperatures destabilize and/or denature Rubisco Activase thereby rendering the enzyme less able or unable to convert inactive Rubisco to the active form. The present invention is directed to Rubisco Activase derived polypeptides with improved thermostability as compared to wild type Rubisco Activase. As such, the photosynthetic process can be made more heat tolerant with the involvement of Rubisco Activase derived polypeptides with improved thermostability.

Any method known in the art can be used to cause plants to express one or more of the Rubisco Activase derived polypeptides of the invention. In one embodiment, transgenic plants can be made to express one or more polypeptides of the invention. The transgenic plant may express the one or more polypeptides of the invention in all tissues (e.g., global expression). Alternatively, the one or more polypeptides of the invention may be expressed in only a subset of tissues (e.g., tissue specific expression), preferably those tissues or organelles involved in photosynthesis (e.g., the plastids). Polypeptides of the invention can be expressed constitutively in the plant or be under the control of an inducible promoter. In some embodiments, the expression and/or activity of the endogenous Rubisco Activase of the plant is reduced or eliminated.

Recombinant Expression

Nucleic acid molecules and polypeptides of the invention can be expressed recombinantly using standard recombinant DNA and molecular cloning techniques that are well known in the art (e.g., Sambrook, Fritsch and Maniatis, *Molecular Cloning: A Laboratory Manual*; Cold Spring Harbor Laboratory Press: Cold Spring Harbor, (1989)). Additionally, recombinant DNA techniques may be used to create nucleic acid constructs suitable for use in making transgenic plants.

Accordingly, an aspect of the invention pertains to vectors, preferably expression vectors, comprising a nucleic acid molecule of the invention or a variant thereof. As used herein, the term "vector" refers to a polynucleotide capable of transporting another nucleic acid to which it has been linked. One type of vector is a "plasmid", which refers to a circular double stranded DNA loop into which additional DNA segments can be introduced. Another type of vector is a viral vector, wherein additional DNA segments can be introduced into the viral genome.

Certain vectors are capable of autonomous replication in a host cell into which they are introduced (e.g., bacterial vectors having a bacterial origin of replication and episomal vectors). Other vectors (e.g., non-episomal vectors) are integrated into the genome of a host cell upon introduction into the host cell, and thereby are replicated along with the host genome. In general, expression vectors of utility in recombinant DNA techniques are often in the form of plasmids (vectors). However, the invention is intended to include such other forms of expression vectors, such as viral vectors (e.g., replication defective retroviruses).

The recombinant expression vectors of the invention comprise a nucleic acid molecule of the invention in a form suitable for expression of the nucleic acid molecule in a host cell. This means that the recombinant expression vectors include one or more regulatory sequences, selected on the basis of the host cells to be used for expression, which is operably associated with the polynucleotide to be expressed. Within a recombinant expression vector, "operably associated" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described in the art (e.g., Goeddel, *Gene Expression Technology: Methods in Enzymology*, (1990) Academic Press, San Diego, Calif.). Regulatory sequences include those which direct constitutive expression of a nucleotide sequence in many types of host cells and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, the area of the organism in which expression is desired, etc. The expression vectors of the invention can be introduced into host cells to thereby produce proteins or peptides, including fusion proteins or peptides, encoded by nucleic acids molecules as described herein.

In some embodiments, isolated nucleic acids which serve as promoter or enhancer elements can be introduced in the appropriate position (generally upstream) of a non-heterologous form of a polynucleotide of the present invention so as to up or down regulate expression of a polynucleotide of the present invention. For example, endogenous promoters can be altered in vivo by mutation, deletion and/or substitution (see, U.S. Pat. No. 5,565,350; International Patent Application Number PCT/US93/03868) or isolated promoters can be introduced into a plant cell in the proper orientation and distance from a cognate gene of a polynucleotide of the present invention so as to control the expression of the gene. Gene expression can be modulated under conditions suitable for plant growth so as to alter the total concentration and/or alter the composition of the polypeptides of the present invention in plant cell. Thus, the present invention provides compositions, and methods for making heterologous promoters and/or enhancers operably linked to a native, endogenous (i.e., non-heterologous) form of a polynucleotide of the present invention.

If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added can be derived from, for example, the nopaline synthase or octopine synthase genes, or alternatively from another plant gene or less preferably from any other eukaryotic gene.

The recombinant expression vectors of the invention can be designed for expression of a polypeptide of the invention in prokaryotic (e.g., Enterobacteriaceae, such as *Escherichia*; Bacillaceae; Rhizoboceae, such as *Rhizobium* and *Rhizobacter*; Spirillaceae, such as photobacterium; *Zymomonas; Serratia; Aeromonas; Vibrio; Desulfovibrio; Spirillum*; Lactobacillaceae; Pseudomonadaceae, such as *Pseudomonas* and *Acetobacter*; Azotobacteraceae and Nitrobacteraceae) or eukaryotic cells (e.g., insect cells using baculovirus expression vectors, yeast cells, plant cells or mammalian cells) (see, Goeddel, supra. for a discussion on suitable host cells). Alternatively, the recombinant expression vector can be transcribed and translated in vitro, for example using T7 promoter regulatory sequences and T7 polymerase.

Expression of proteins in prokaryotes is most often carried out in *E. coli* with vectors comprising constitutive or inducible promoters directing the expression of either fusion or non-fusion proteins. Fusion vectors add a number of amino acids to a protein encoded therein, usually to the amino terminus of the recombinant protein. Such fusion vectors typically serve at least three purposes: 1) to increase expression of the recombinant protein; 2) to increase the solubility of the recombinant protein and/or 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson, (1988) *Gene* 67:31-40), pMAL (New England Biolabs, Beverly, Mass.) and pRIT5 (Pharmacia, Piscataway, N.J.) which fuse glutathione S-transferase (GST), maltose E binding protein or protein A, respectively, to the target recombinant protein.

In another embodiment, the expression vector is a yeast expression vector. Examples of vectors for expression in yeast *S. cerevisiae* include pYepSec1 (Baldari, et al., (1987) *EMBO J.* 6:229-234), pMFa (Kurjan and Herskowitz, (1982) *Cell* 30:933-943), pJRY88 (Schultz, et al., (1987) *Gene* 54:113-123), pYES2 (Invitrogen Corp., San Diego, Calif.), and pPicZ (Invitrogen Corp., San Diego, Calif.).

Alternatively, the expression vector is a baculovirus expression vector. Baculovirus vectors available for expression of proteins in cultured insect cells (e.g., Sf 9 cells) include the pAc series (Smith, et al., (1983) *Mol. Cell Biol.* 3:2156-2165) and the pVL series (Lucklow and Summers, (1989) *Virology* 170:31-39).

In yet another embodiment, a nucleic acid molecule of the invention is expressed in plant cells using a plant expression vector including, but not limited to, tobacco mosaic virus and potato virus expression vectors.

Other suitable expression systems for both prokaryotic and eukaryotic cells are known in the art (see, e.g., chapters 16 and 17 of Sambrook, et al., (1990) *Molecular Cloning, A Laboratory Manual*, 2d Ed., Cold Spring Harbor Laboratory, Cold Spring Harbor, N.Y.).

A number of promoters can be used in the practice of the invention. The promoters can be selected based on the desired outcome. The nucleic acids can be combined with constitutive, tissue-specific, inducible or other promoters for expression in the host organism.

A "tissue-specific promoter" may direct expression of nucleic acids of the present invention in a specific tissue, organ or cell type. Tissue-specific promoters can be inducible. Similarly, tissue-specific promoters may only promote transcription within a certain time frame or developmental stage within that tissue. Other tissue specific promoters may be active throughout the life cycle of a particular tissue. One of ordinary skill in the art will recognize that a tissue-specific promoter may drive expression of operably linked sequences in tissues other than the target tissue. Thus, as used herein, a tissue-specific promoter is one that drives expression preferentially in the target tissue or cell type, but may also lead to some expression in other tissues as well. A number of tissue-specific promoters can be used in the present invention. With the appropriate promoter, any organ can be targeted, such as shoot vegetative organs/structures (e.g., leaves, stems and tubers), roots, flowers and floral organs/structures (e.g., bracts, sepals, petals, stamens, carpels, anthers and ovules), seed (including embryo, endosperm and seed coat) and fruit. For instance, promoters that direct expression of nucleic acid molecules in leaves and/or photosynthetic organ-specific promoters (such as the RBCS promoter disclosed in Khoudi, et al., (1997) *Gene* 197:343) are useful for enhancing photosynthesis. Additionally, tissue specific expression can be obtained by adding a peptide onto a polypeptide of the invention that directs localization of the attached polypeptide to the photosynthetic organs (such as those disclosed in U.S. patent application Ser. No. 11/150,054).

A "constitutive promoter" is defined as a promoter which will direct expression of a gene in all tissues and are active under most environmental conditions and states of development or cell differentiation. Examples of constitutive promoters include the cauliflower mosaic virus (CaMV) 35S transcription initiation region, the 1'- or 2'-promoter derived from T-DNA of *Agrobacterium tumafaciens*, and other transcription initiation regions from various plant genes known to those of ordinary skill in the art. Such genes include for example, ACT11 from *Arabidopsis* (Huang, et al., (1996) *Plant Mol. Biol.* 33:125-139), Cat3 from *Arabidopsis* (GenBank Accession Number U43147, Zhong, et al., (1996) *Mol. Gen. Genet.* 251:196-203), the gene encoding stearoyl-acyl carrier protein desaturase from *Brassica napus* (Genbank Accession Number X74782, Solocombe, et al., (1994) *Plant Physiol.* 104:1167-1176), GPc1 from maize (GenBank Accession Number X15596, Martinez, et al., (1989) *J. Mol. Biol.* 208:551-565), and Gpc2 from maize (GenBank Accession Number U45855, Manjunath, et al., (1997) *Plant Mol. Biol.* 33:97-112). Any strong, constitutive promoter, such as the CaMV 35S promoter, can be used for the expression of polynucleotides of the present invention throughout the plant.

The term "inducible promoter" refers to a promoter that is under precise environmental or developmental control. Examples of environmental conditions that may effect transcription by inducible promoters include anaerobic conditions, elevated temperature, the presence of light or spraying with chemicals/hormones.

Suitable constitutive promoters for use in a plant host cell include, for example, the core promoter of the Rsyn7 promoter and other related constitutive promoters (International Publication Number WO 1999/43838 and U.S. Pat. No. 6,072,050); the core CaMV 35S promoter (Odell, et al., (1985) *Nature* 313:810-812); rice actin (McElroy, et al., (1990) *Plant Cell* 2:163-171); ubiquitin (Christensen, et al., (1989) *Plant Mol. Biol.* 12:619-632 and Christensen, et al., (1992) *Plant Mol. Biol.* 18:675-689); pEMU (Last, et al., (1991) *Theor. Appl. Genet.* 81:581-588); MAS (Velten, et al., (1984) *EMBO J.* 3:2723-2730); ALS promoter (U.S. Pat. No. 5,659,026) and the like (e.g., U.S. Pat. Nos. 5,608,149; 5,608,144; 5,604,121; 5,569,597; 5,466,785; 5,399,680; 5,268,463; 5,608,142 and 6,177,611).

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

Accordingly, the present invention provides a host cell having an expression vector comprising a nucleic acid molecule of the invention, or a variant thereof. A host cell can be any prokaryotic (e.g., *E. coli, Bacillus thuringiensis*) or eukaryotic cell (e.g., insect cells, yeast or plant cells). The invention also provides a method for expressing a nucleic acid molecule of the invention thus making the encoded polypeptide comprising the steps of i) culturing a cell comprising a nucleic acid molecule of the invention under conditions that allow production of the encoded polypeptide; and ii) isolating the expressed polypeptide.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid molecules into a host cell, including calcium phosphate or calcium chloride co-precipitation, DEAE-dextran-mediated transfection, lipofection, electroporation, *Agrobacterium tumefaciens* and vacuum infiltration. Suitable methods for transforming or transfecting host cells can be found in the art (e.g., Sambrook, et al., supra.)

Production of Transgenic Plants

Any method known in the art can be used for transforming a plant or plant cell with a nucleic acid molecule of the present invention. Nucleic acid molecules can be incorporated into plant DNA (e.g., genomic DNA or chloroplast DNA) or be maintained without insertion into the plant DNA (e.g., through the use of artificial chromosomes). Suitable methods of introducing nucleic acid molecules into plant cells include microinjection (Crossway, et al., (1986) *Biotechniques* 4:320-334); electroporation (Riggs, et al., (1986) *Proc. Natl. Acad. Sci.* 83:5602-5606; D'Halluin, et al., (1992) *Plant Cell* 4:1495-1505); *Agrobacterium*-mediated transformation (U.S. Pat. Nos. 5,563,055 and 5,981,840, Osjoda, et al., (1996) *Nature Biotechnology* 14:745-750; Horsch, et al., (1984) *Science* 233:496-498; Fraley, et al., (1983) *Proc. Natl. Acad. Sci.* 80:4803; and *Gene Transfer to Plants*, Potrykus, ed., Springer-Verlag, Berlin 1995); direct gene transfer (Paszkowski, et al., (1984) *EMBO J.* 3:2717-2722); ballistic particle acceleration (U.S. Pat. Nos. 4,945,050; 5,879,918; 5,886,244; 5,932,782; Tomes, et al., (1995) "Direct DNA Transfer into Intact Plant Cells via Microprojectile Bombardment, in *Plant Cell, Tissue, and Organ Culture: Fundamental Methods*, ed. Gamborg and Phillips, Springer-Verlag, Berlin; and McCabe, et al., (1988) *Biotechnology* 6:923-926); virus-mediated transformation (U.S. Pat. Nos. 5,889,191, 5,889, 190, 5,866,785, 5,589,367 and 5,316,931); pollen transformation (De Wet, et al., (1985) in *The Experimental Manipulation of Ovule Tissues*, ed. Chapman, et al., Longman, New York, pp. 197-209); Lec 1 transformation (U.S. patent application Ser. No. 09/435,054; International Patent Publication Number WO 2000/28058); whisker-mediated transformation (Kaeppler, et al., (1990) *Plant Cell Reports* 9:415-418; Kaeppler, et al., (1992) *Theor. Appl. Genet.* 84:560-566) and chloroplast transformation technology (Bogorad, (2000) *Trends in Biotechnology* 18:257-263; Ramesh, et al., (2004) *Methods Mol Biol.* 274:301-7; Hou, et al., (2003) *Transgenic Res.* 12:111-4; Kindle, et al., (1991) *Proc. Natl. Acad. Sci.* 88:1721-5; Bateman and Purton, (2000) *Mol Gen Genet.* 263:404-10; Sidorov, et al., (1999) *Plant J.* 19:209-216).

The choice of transformation protocols used for generating transgenic plants and plant cells can vary depending on the type of plant or plant cell, i.e., monocot or dicot, targeted for transformation. Examples of transformation protocols particularly suited for a particular plant type include those for: potato (Tu, et al., (1998) *Plant Molecular Biology* 37:829-838; Chong, et al., (2000) *Transgenic Research* 9:71-78); soybean (Christou, et al., (1988) *Plant Physiol.* 87:671-674; McCabe, et al., (1988) *BioTechnology* 6:923-926; Finer and McMullen, (1991) *In Vitro Cell Dev. Biol.* 27P:175-182; Singh, et al., (1998) *Theor. Appl. Genet.* 96:319-324); maize (Klein, et al., (1988) *Proc. Natl. Acad. Sci.* 85:4305-4309; Klein, et al., (1988) *Biotechnology* 6:559-563; Klein, et al., (1988) *Plant Physiol.* 91:440-444; Fromm, et al., (1990) *Biotechnology* 8:833-839; Tomes, et al., (1995) "Direct DNA Transfer into Intact Plant Cells via Microprojectile Bombardment," in *Plant Cell, Tissue, and Organ Culture: Fundamental Methods*, ed. Gamborg (Springer-Verlag, Berlin)); cereals (Hooykaas-Van Slogteren, et al., (1984) *Nature* 311:763-764; U.S. Pat. No. 5,736,369).

In some embodiments, more than one construct is used for transformation in the generation of transgenic plants and plant cells. Multiple constructs may be included in cis or trans positions. In preferred embodiments, each construct has a promoter and other regulatory sequences.

The transgenic plants can express the transgene in any way known in the art including, but not limited to, constitutive expression, developmentally regulated expression, and tissue specific expression. In a specific embodiment, promoters that direct expression of nucleic acid molecules in leaves and/or photosynthetic organs (such as the RBCS promoter disclosed in Khoudi, et al., *Gene* 197:343) are used to express the nucleic acid molecules and/or polypeptides of the invention.

Transformed plant cells which are derived by any of the above transformation techniques can be cultured to regenerate a whole plant which possesses the transformed genotype and thus the desired phenotype. Such regeneration techniques rely on manipulation of certain phytohormones in a tissue culture growth medium, typically relying on a biocide and/or herbicide marker that has been introduced together with the desired nucleotide sequences. Plant regeneration from cultured protoplasts is described in the art (e.g., Evans, et al., *Protoplasts Isolation and Culture, Handbook of Plant Cell Culture*, pp. 124-176, MacMillilan Publishing Company, New York, 1983; and Binding, Regeneration of Plants, Plant Protoplasts, pp. 21-73, CRC Press, Boca Raton, 1985). Regeneration can also be obtained from plant callus, explants, organs or parts thereof. Such regeneration techniques are also described in the art (e.g., Klee, et al., (1987) *Ann. Rev. of Plant Phys* 38:467-486).

The term "plant" includes whole plants, shoot vegetative organs/structures (e.g. leaves, stems and tubers), roots, flowers and floral organs/structures (e.g. bracts, sepals, petals, stamens, carpels, anthers and ovules), seed (including embryo, endosperm and seed coat) and fruit (the mature ovary), plant tissue (e.g. vascular tissue, ground tissue and the like) and cells (e.g. guard cells, egg cells, trichomes and the like) and progeny of same. The class of plants that can be used in methods of the present invention includes the class of higher and lower plants amenable to transformation techniques, including angiosperms (monocotyledonous and dicotyledonous plants), gymnosperms, ferns and multicellular algae. Plants of a variety of ploidy levels, including aneuploid, polyploid, diploid, haploid and hemizygous plants are also included.

The nucleic acid molecules of the invention can be used to confer desired traits on essentially any plant. Thus, the invention has use over a broad range of plants, including species from the genera *Agrotis, Allium, Ananas, Anacardium, Apium, Arachis, Asparagus, Athamantha, Atropa, Avena, Bambusa, Beta, Brassica, Bromus, Browaalia, Camellia, Cannabis, Carica, Ceratonia. Cicer, Chenopodium, Chicorium, Citrus, Citrullus, Capsicum, Carthamus, Cocos, Coffea, Coix, Cucumis, Cucurbita, Cynodon, Dactylis, Datura, Daucus, Dianthus, Digitalis, Dioscorea, Elaeis, Eliusine, Euphorbia, Festuca, Ficus, Fragaria, Geranium, Glycine,*

*Graminae, Gossypium, Helianthus, Heterocallis, Hevea, Hibiscus, Hordeum, Hyoscyamus, Ipomoea, Lactuca, Lathyrus, Lens, Lilium, Linum, Lolium, Lotus, Lupinus, Lycopersicon, Macadamia, Macrophylla, Malus, Mangifera, Manihot, Majorana, Medicago, Musa, Narcissus, Nemesia, Nicotiana, Onobrychis, Olea, Olyreae, Oryza, Panicum, Panicum, Panieum, Pannisetum, Pennisetum, Petunia, Pelargonium, Persea, Pharoideae, Phaseolus, Phleum, Picea, Poa, Pinus, Pistachia, Pisum, Populus, Pseudotsuga, Pyrus, Prunus, Pseutotsuga, Psidium, Quercus, Ranunculus, Raphanus, Ribes, Ricinus, Rhododendron, Rosa, Saccharum, Salpiglossis, Secale, Senecio, Setaria, Sequoia, Sinapis, Solanum, Sorghum, Stenotaphrum, Theobromus, Trigonella, Trifolium, Trigonella, Triticum, Tsuga, Tulipa, Vicia, Vitis, Vigna* and *Zea*.

In specific embodiments, transgenic plants are maize, tomato, potato, rice, soybean, cotton, sunflower, alfalfa, lettuce, canola, sorghum or tobacco plants.

Transgenic plants may be grown and pollinated with either the same transformed strain or different strains. Two or more generations of the plants may be grown to ensure that expression of the desired nucleic acid molecule, polypeptide and/or phenotypic characteristic is stably maintained and inherited. One of ordinary skill in the art will recognize that after the nucleic acid molecule of the present invention is stably incorporated in transgenic plants and confirmed to be operable, it can be introduced into other plants by sexual crossing. Any of a number of standard breeding techniques can be used, depending upon the species to be crossed.

Determination of Expression in Transgenic Plants

Any method known in the art can be used for determining the level of expression in a plant of a nucleic acid molecule of the invention or polypeptide encoded therefrom. For example, the expression level in a plant of a polypeptide encoded by a nucleic acid molecule of the invention can be determined using molecular techniques including, but not limited to, immunoassay, immunoprecipitation, gel electrophoresis and quantitative gel electrophoresis.

Additionally, the expression level in a plant of a polypeptide encoded by a nucleic acid molecule of the invention can be determined by the degree to which the plant phenotype (including, but not limited to, photosynthesis rates, growth rates, and seed yield) is altered under heated conditions compared to plants expressing wild type Rubisco Activase.

Furthermore, extracts or polypeptides isolated from transgenic plants, tissues thereof, or cells thereof can be used in in vitro assays.

The contents of all published articles, books, reference manuals and abstracts cited herein, are hereby incorporated by reference in their entirety to more fully describe the state of the art to which the invention pertains.

As various changes can be made in the above-described subject matter without departing from the scope and spirit of the present invention, it is intended that all subject matter contained in the above description and/or defined in the appended claims, be interpreted as descriptive and illustrative of the present invention. Modifications and variations of the present invention are possible in light of the above teachings.

EXAMPLES

Example 1

Isolating Rubisco Activase Derived Polypeptides

Rubisco Activase libraries were generated from single gene shuffling (see, e.g., Crameri, et al., (1998) *Nature*. 391 (6664):288-91; Chang, et al., (1999) *Nat Biotechnol*. 17(8): 793-7; Ness, et al., (1999) *Nat Biotechnol*. 17(9):893-6; Christians, et al., (1999) *Nat Biotechnol*. 17(3):259-64 and U.S. Pat. Nos. 6,605,430; 6,117,679 and 5,605,793) and synthetic shuffling (see, e.g., U.S. Pat. No. 6,436,675 and International Publication Numbers WO 2000/42561; WO 2001/23401; WO 2000/42560; and WO 2000/42559) using wild type Rubisco Activase of SEQ ID NO: 1 as a template.

Briefly, *Arabidopsis* RNA was isolated from green leaves using Trizol® reagent according to the manufacturer's protocol (Invitrogen). RCA cDNA (GenBank accession number NM 179990) was PCR cloned into TOPO® vector (Invitrogen) using TITANIUM™ one-step RT-PCR Kit (BD Biosciences-Clontech). For single gene shuffling in the first round, the mature RCA short form (coding region V59 to K438) was PCR amplified (Qiagen Taq DNA polymerase or Stratagene Mutazyme DNA polymerase), fragmented and reassembled in a primerless PCR reaction and the shuffled genes were then rescued with flanking primers that contain an NcoI site (5') and a BamHI site, 6x-His coding region and a stop codon (3'). The library of variants was cloned into an *E. coli* expression vector (pET16b, Novagen) digested with NcoI and BamHI. To increase pool of genetic in the first round, synthetic shuffling was carried out using diversity from wheat, rice, cotton, spinach and cucumber (see, Ness, et al., (2002) *Nat Biotechnol*. 20:1251-1255). A second round of gene shuffling using first round variants as parents was performed as previously described by Crameri, et al., (1998) *Nature* 15:288-291.

Rubisco Activase derived polypeptides with improved thermostability were isolated by the following screening methodology.

First Tier: Rubisco Activation Assay.

Cultures of *E. coli* expressing a Rubisco Activase derived polypeptide were pelleted at 4° C., 3,500 rpm for 15 minutes and stored in a 96-well V-bottom PCR-plate at −80° C. *E. coli* cell lysate was prepared by thawing the cultures at room temperature for 5 minutes, adding 75 µl Sonication buffer (100 mM Tricine KOH pH 8.0; 20 mM ascorbate; 3 mM Mg-ATP; 10 mM $MgCl_2$; 10% v/v glycerol; 10 mM βme; ×3.33 protease inhibitor; 1 µl/ml benzonase; 1 mg/ml lysosyme) to each well and shaking the plate for 60 minutes at 4° C. until the pellet was lysed. The plates were sonicated with MISONIX microplate sonicator for 1 minute and then cooled for 1 minute. This process was repeated four times. The cultures were centrifuged at 4,000 rpm for 20 minutes at 4° C. The supernatant that contained soluble protein was used in the Rubisco activation assays.

Twenty-two µl of the *E. coli* supernatant was transferred to a 96-well U-bottom scintillation-plate and incubated at room temperature for 15 minutes (and used as the lysate for "normal conditions" in the assays). Heat treatment of the lysate was performed by transferring 35 µl of the *E. coli* supernatant to a 96-well V-bottom PCR-plate and incubating at 40° C. for 15 minutes. The heat treated supernatant was then transferred to a 96-well U-bottom scintillation-plate (and used as the lysate for "heat treated conditions" in the assays). Both plates were incubated for 5 minutes at 4° C. before assay performance.

Rubisco activation was assayed by incubating the cell lysate containing Rubisco Activase or a Rubisco Activase derived polypeptide with purified deactivated *Arabidopsis* Rubisco (15 µg) in reaction buffer (100 mM Tricine KOH pH 8.0; 10 mM $MgCl_2$; 10 mM [$^{14}C$]$NaHCO_3$; Mg-ATP; 4 mM RuBP; 1 mM PEP; 40 µg/ml pyruvate kinase) at room temperature for 15 minutes (see, Shen, et al., (1991) *J. Biol. Chem*. 266:8963-8968). The activation of Rubisco by cell lysate expressing Rubisco Activase derived polypeptides was terminated by addition of 1 N HCl, and the incorporation of $^{14}CO_2$ determined by liquid scintillation spectroscopy.

The Rubisco used in the above-described assay was purified from *Arabidopsis* leaves. The leaves were homogenized and frozen in liquid nitrogen before resuspension in extraction buffer (100 mM Hepes-KOH pH 8.0; 1 mM EDTA pH 8.0; 3 mM DDT; 0.5 mM PMSF; 10 mM $MgCl_2$; 10 mM $NaHCO_3$). The suspension was centrifuged at 12,000 rpm for 20 min at 4° C. and the supernatant was collected. The supernatant was kept on ice under continuous stirring while ammonium sulfate was added to a final concentration of 35% of saturation and centrifuged at 12,000 rpm for 20 min at 4° C. The supernatant was stirred for an additional 30 min. with ammonium sulfate to a final concentration of 55% of saturation before centrifugation at 12,000 rpm for 20 min at 4° C. The pellet was dissolved in extraction buffer and further precipitated with 18% polyethylene glycol and centrifugation. The pellet was resuspended in extraction buffer (about 1 ml/original 40 ml of supernatant) and centrifuged at 13,000 rpm for 30 min at 4° C. The purified Rubisco was in the supernatant and glycerol was added to a final concentration of 10%.

The purified Rubisco was deactivated by the following protocol (see, Wang, et al., (1992) *Plant Physiol.* 100:1858-1862). Ten mM of DTT was added to the purified Rubisco and incubated at 45° C. for 10 min. One ml of the mixture was added to a 20 ml Sephadex G-50 column equilibrated with equilibration buffer (50 mM Tricine-KOH pH 8.0 and 0.5 mM EDTA pH 8.0). Deactivated Rubisco was eluted from the column by the addition of 1 ml fractions of equilibration buffer. The eluted deactivated Rubisco was collected and incubated at room temperature to 1 hour before incubation on ice for one hour in the presence of 4 mM RuBp.

Second Tier: HTP Temperature Profile of Rubisco Activation by Cell Lysate of Active Clones.

Clones of interest identified in the first tier screening were further characterized in the second tier of screening. Cell lysate from each active clone was retested as described above except that the temperature treatment was carried out at four different temperatures (16° C., 25° C., 40° C. and 45° C.) prior to assay. Clones that possessed relatively improved thermostability profile compare to wide type Rubisco Activase (SEQ ID NO: 2) were selected for $3^{rd}$ tier screening.

Third Tier: Temperature Profile of Rubisco Activation by Purified Rubisco Activase Variants.

In order to determine the specific activity of the derived polypeptides identified by the first two tiers of screening, affinity purified polypeptides were pre-incubated at different temperatures and then analyzed for their ability to activate Rubisco at 25° C. Since Rubisco Activase catalyses deactivated Rubisco in a time dependent manner, each reaction was monitored for 15 minutes in 3-minute intervals. The ratio of Rubisco Activase: Rubisco was set to 1:40 similarly to the ratio in plant leaves. The thermostability of wild type Rubisco Activase (SEQ ID NO: 2) and Rubisco Activase derived polypeptides is shown in Table 2. The percent thermostability represents the amount of Rubisco that has been activated by Rubisco Activase at 40° C. as a percent of the amount of Rubisco that has been activated by Rubisco Activase at 25° C.

Example 2

In Vitro Characterization of Rubisco Activase Derived Polypeptides

The Rubisco Activase derived polypeptides isolated in Example 6.1 were tested in vitro in three different assays in order to determine the specific activity at 25° C. and 40° C. and their thermostability (t.s.). In all cases, the results obtained with wild type Rubisco Activase at 25° C. were set to 100%.

Activation of Deactivated Rubisco.

Purified Rubisco Activase derived polypeptides were assayed as described in the first tier assay of Example 1 except that the derived polypeptides were incubated at 40° C. or 45° C. for 15, 30, 45 or 60 minutes prior to performance of the Rubisco activation assay. Results are shown in columns 2-4 of Table 3. Column 2 of Table 3 represents the amount of activated Rubisco that is obtained after incubation of deactivated Rubisco with Rubisco Activase at 25° C. There were no heated conditions used. Column 3 of Table 3 represents the amount of Rubisco that has been activated by Rubisco Activase after a 15 min 40° C. heat treatment as a percent of the amount of Rubisco that has been activated by Rubisco Activase at 25° C. Column 4 of Table 3 represents the amount of Rubisco that has been activated by Rubisco Activase with a 45 min 40° C. heat treatment as a percent of the amount of Rubisco that has been activated by Rubisco Activase with no heat treatment (at 25° C.).

Rubisco activation by Rubisco Activase derived polypeptides 301C7 and 382D8 exhibit high thermostability at 40° C. and 45° C. treatments (FIG. 1A). The activity of 382D8 after 45° C. treatment was 80% higher than RCA1 at the same temperature treatment and only 10% less than the activity of RCA1 incubated at 25° C.

Rubisco Activation Under Catalytic Conditions.

Purified Rubisco Activase derived polypeptides were assayed as described in the first tier assay of Example 1 except that the assay was performed under heated conditions (i.e., 40° C.) (Crafts-Brandner and Salvucci, (2000) PNAS 97:13430-13435). Results are shown in columns 5-6 of Table 3. Column 5 of Table 3 represents the amount of activated Rubisco that is obtained after incubation of deactivated Rubisco with Rubisco Activase at 25° C. There were no heated conditions used. Column 6 of Table 3 represents the amount of Rubisco that has been activated by Rubisco Activase when the assay is conducted at 40° C. as a percent of the amount of Rubisco that has been activated by Rubisco Activase when the assay is conducted at 25° C.

Wild-type RCA maintained a Rubisco activation state of 0.5 at 40° C. while Rubisco Activase derived polypeptides 183H12, 301C7 and 382D8 were able to maintain activation states of 0.62-0.72 under the same conditions (FIG. 1B). Relative to reactions at 25° C., the activation state of Rubisco maintained by the thermostable variants at 40° C. was in the range of 78-98% versus 70% for the wild type enzyme. The protein displaying the highest specific activity at either 25° C. or 40° C. was the best variant isolated in the first round, 183H12.

ATPase Activity.

Since Rubisco Activase is an ATPase (the polypeptide contains the $AAA^+$ domain) that requires ATP to loosen the binding of Rubisco to sugar phosphates, the effect of temperature on ATP hydrolysis by Rubisco Activase was tested. The ATPase assay that monitored the intrinsic activity of the activase complex regardless of its interaction with Rubisco is commonly used for Rubisco Activase characterization. ATPase assay has been performed as described by Salvucci ((1992) *Arch. Biochem. Biophys.* 298:688-696). Results are shown in columns 7-8 of Table 3. Column 7 of Table 3 represents the amount of hydrolyzed ATP that is present after incubation of Rubisco Activase with ATP at 25° C. There were no heated conditions used. Column 8 of Table 3 represents the amount of hydrolyzed ATP that is present after incubation with Rubisco Activase that had been heat treated at 40° C. as a percent of the amount of hydrolyzed ATP that is present after incubation with Rubisco Activase that had not been heat treated.

FIG. 1C shows that the stability of Rubisco Activase derived polypeptides 301C7 and 382D8 at 35° C. and 40° C. was improved more than 10-fold compared to RCA1, whereas 183H12 exhibited 20% and 30% improvement at 25° C. and 40° C., respectively.

Example 3

Complementation of Rubisco Activase Deletion Mutant

In order to express shuffled variants in homozygous background for the deletion (Δrca/☐Δrca) (see, Li, et al., (2001) Plant J. 27:235-242) the following complementation cascade was developed: 1) Selection of heterozygous plants for the deletion by HTP-PCR using single-leaf 96-well DNA extraction method (Xin, et al., (2003) BioTechniques 34:820-826), with specific primers for the wild-type and deleted alleles. 2) Transformation with the gene of interest. 3) TO selection for antibiotic resistance and PCR analysis for homozygosity. 4) Self pollination of the resultant homozygous plants in order to obtain T1 transgenic lines.

Figure 2:
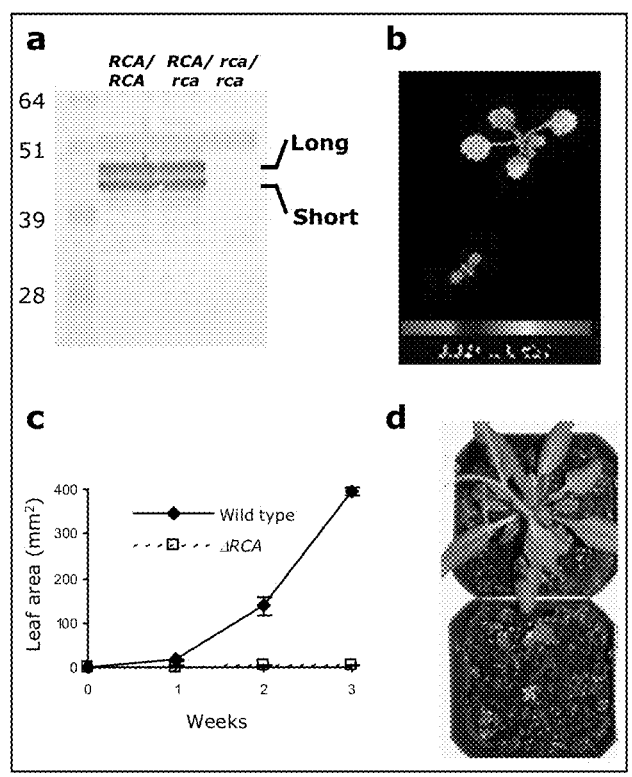
FIGS. 2A-2D: Characterization of the Rubisco Activase mutant (Δrca) at ambient $CO_2$. (A) Immuno blot analysis from leaves of *Arabidopsis* wild-type (RCA/RCA), heterozygous (RCA/Δrca) and homozygous (Δrca/Δrca) plants. The blot was immunodecorated with polyclonal antibodies raised against the recombinant *Arabidopsis* RCA1. (B) Photosynthetic performance of three-week old wild-type (upper) and Δrca (lower) plants as measured using fluorescence image analysis. (C) Leaf area of the plants described in (B) (50 plants per phenotype) at the indicted age. (D) Photograph of eight week old wild-type (upper) and Δrca (lower) plants.

Immunoblot analysis of wild-type, heterozygous and homozygous plants (genetic background RCA/RCA, RCA/Δrca and Δrca/Δrca respectively) revealed that the gene products (long and short forms) were expressed at similar levels in wild-type and heterozygous plants (FIG. 2A). The absence of the short and long isoforms in plants homozygous for the deletion confirmed that the mutation abrogates the expression of both RCA1 and RCA2. Δrca plants grown at ambient $CO_2$ exhibited low photosynthetic performance (Fq'/Fm' values) compared to wild-type (0.185±0.038 and 0.332±0.033 respectively) (FIG. 2B) and significant lower leaf area after 3 weeks on soil (2.93±0.49 and 395.4±8.75 $mm^2$ respectively) (FIG. 2C). Two-month old Δrca homozygotes were severely stunted and chlorotic by comparison to wild-type plants (FIG. 2D).

Figure 3:
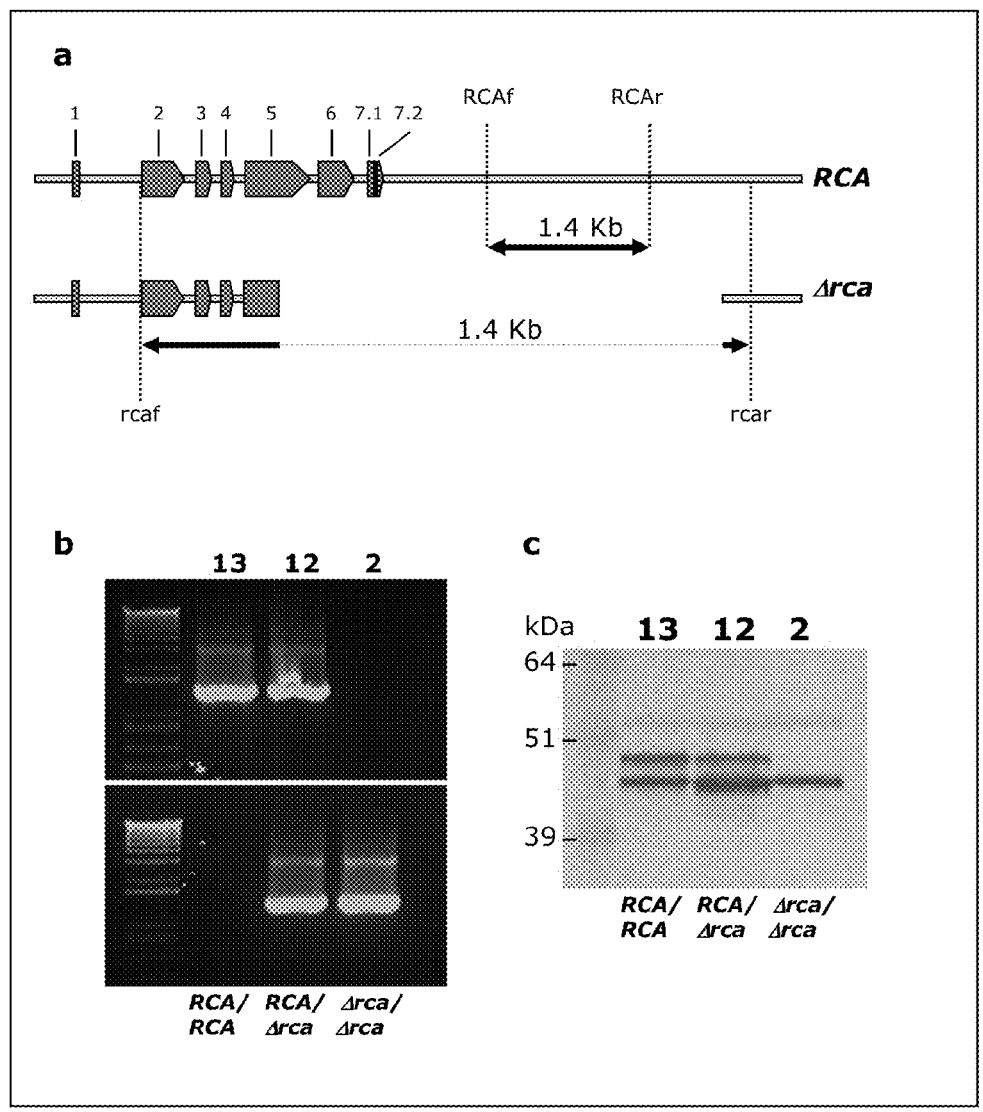
FIGS. 3A-3C: Molecular characterization of Δrca mutant. (A) Schematic map of the wild-type (RCA) and deletion (Δrca) alleles. Numbers indicate the RCA exons. The forward and reverse primers for amplification of the 1.4 kb PCR products of RCA (RCAf and RCAr) and Δrca (rcaf and rcar) alleles are indicated. (B) PCR analysis (RCA primers-upper panel; rca primers-bottom panel) of T1 plants expressing 183H12. Lines number (up) and genetic background (down) are indicated. (C) Western blot analysis of total protein (5 µg/lane) from leaves of the lines described in (B). The blot was probed with polyclonal antibodies raised against the recombinant RCA1.

Based on sequence analysis and mapping of the deleted fragment, two sets of primers were designed: RCA primers (forward 5'-CAGACAATGTTGGCCTC-3' (SEQ ID NO: 23) and reverse 5'-ACGAGTAACGATGGTAGG-3' (SEQ ID NO: 24)) specific for the wild-type allele that give 1.5 kb product, and rca primers (forward 5'-GTCTATACCT-TGAGC-3' (SEQ ID NO: 25) and reverse 5'-TCAGTCAT-ACTCGG-3' (SEQ ID NO: 26)) that give 1.5 kb product in the deleted allele and 4.9 kb in the wild-type allele (FIG. 3A). In order to amplify the 1.5 kb product with the rca primers but not the 4.9 kb, the PCR amplification cycle was set to 1.5 min. Those two sets of primers were utilized to characterize the genetic background of the T1 plants. Since the transformation host was heterozygous for deletion of the endogenous rca locus, the T1 plants expressing the Rubisco activase transgenes are a mixture of wild-type (RCA/RCA) heterozygotes (RCA/Δrca) and homozygotes (Δrca/Δrca). Transgenic lines expressing the shuffled variant 183H12 in the different genetic backgrounds have been identified using PCR screening (FIG. 3B) and immunoblot analysis (FIG. 3C). Plants that express 183H12 in genetic backgrounds containing at least one wild type allele (#13; wt, #12; heterozygous for the deletion) have both the short and the long forms of the protein. In line #2 (homozygous for the deletion) only the short form was detected because the transgene was designed to express only the short form of the protein.

Example 4

In Planta Characterization of Rubisco Activase Derived Polypeptides

To determine the effect of improved Rubisco Activase under normal and increased temperatures, the Arabidopsis Rubisco Activase deletion mutant (Δrca) (see, Example 3). Δrca was functionally complemented with wide type Rubisco Activase (SEQ ID NO: 1), $1^{st}$ round Rubisco Activase derived polypeptide 183H12 (SEQ ID NO: 7) and two $2^{nd}$ round Rubisco Activase derived polypeptides 382D8 (SEQ ID NO: 15) and 301C7 (SEQ ID NO: 19).

In order to express the wild type Rubisco Activase and the Rubisco Activase derived polypeptides in transgenic Arabidopsis plants (Δrca), the transgenes encoding the chloroplast transit peptide and the coding region of rca1 or the derived polypeptides were cloned into pMAXY4384 that contains the Mirabilis Mosaic Caulimovirus promoter (MMV) with a double enhancer domain (Day and Maiti, (1999) Transgenics 3:61-70), the UBQ3 terminator and the kanamycin resistance gene nptII. Heterozygous Deleteagene™ RCA mutants were transformed by Agrobacterium tumefaciens strain GV3101 using the floral dipping method (Clough, et al., (1998) Plant J. 16:735-743). To confirm expression, protein was extracted from plant tissue (2-3 g fresh weight) in liquid $N_2$ and 1 ml of extraction buffer (100 mM Tricine-KOH pH 8, EDTA pH 8, 10 mM 2-mercaptoethanol, and Protease inhibitor cocktail Set V). The crude extract was clarified by successive centrifugation for 5 min at 3000 g, and 20 min at 12,000 g. Ten micrograms of soluble protein extract was separated on 10% SDS-polyacrylamide gels and transferred to a nitrocellulose membrane (according to the instructions supplied by Invitrogen). The blot was immunodecorated with the polyclonal antibodies raised against the recombinant Arabidopsis RCA1 and the proteins were detected using the Ap conjugated substrate kit (Bio-Rad).

Figure 4:
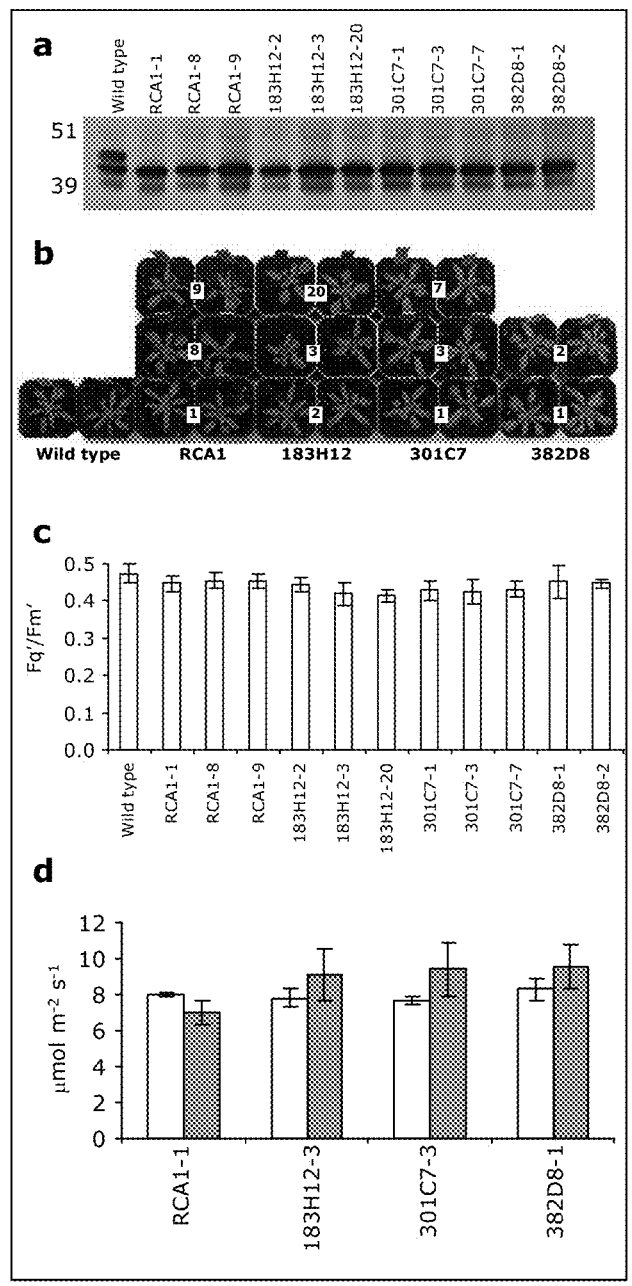
FIGS. 4A-4D: Functional complementation of Δrca mutants expressing RCA1 and thermostable variants 183H12, 301C7 and 382D8 under normal growth conditions (22° C.). Numbers indicate the line designations of independent transformation events. (A) Immuno blot analysis of total protein from three-week old leaves. (B) Photographs depicting the similar size of all the plants described above when grown under normal conditions. (C) Photosynthetic performance of the plants (8 to 10 plants/independent line) described above monitored by fluorescence image analysis. (D) Effect of temporary (1 hr) moderate heat stress treatment on photosynthetic rates of Δrca transgenic lines expressing RCA1 and thermostable variants. The net photosynthesis of four independent plants per line was monitored using an infrared gas analyzer at 22° C. (white) and 30° C. (gray).

As shown in FIG. 4A, wild-type plants (RCA/RCA) expressed short and long isoforms of activase, whereas transgenic Δrca lines complemented by the transgenes expressed only the 43 kDa short isoform. Under 22° C. culture conditions (plants grown in 16 hour light (225 μmol photons $m^{-2}$ $s^{-1}$)/8 hour dark cycles), the transgenic lines exhibited similar growth rates as the wild-type untransformed plants (FIG. 4B). Photosynthetic performance (photosystem II operating efficiency Fq'/Fm') and growth rates were analyzed using the chlorophyll a fluorescence imaging system (FluorImager, Qubit Systems) as previously described (Baker, et al., (2001) J Exp. Bot. 52:615-621). The Fq'/Fm' values of transgenic deletion lines expressing RCA1 or Rubisco Activase derived polypeptides 183H12, 301C7 or 382D8 (ΔrcaRCA1, Δrca183H12, Δrca301C7 and Δrca382D8, respectively) were similar to wild-type untransformed plants, indicating that expression of the short form is sufficient for functional complementation of Δrca under normal growth conditions (FIG. 4C). Under these conditions the photosynthetic activity measured by the portable infrared gas analyzer (LI6400, Li-Cor) under 150 μmol photons $m^{-2}$ $s^{-1}$ and 350 μbar $CO_2$. of ΔrcaRCA1-1 was similar to Δrca183H12-3, Δrca301C7-3 and Δrca382D8-1 (FIG. 4D). Temporary exposure to 30° C. for 1 hr resulted in 12% decreased photosynthesis in ΔrcaRCA1-1. Conversely, lines Δrca183H12-3, Δrca301C7-3 and Δrca382D8-1 showed 16, 22 and 16% increased photosynthesis after 1 hr at 30° C.

Figure 5:
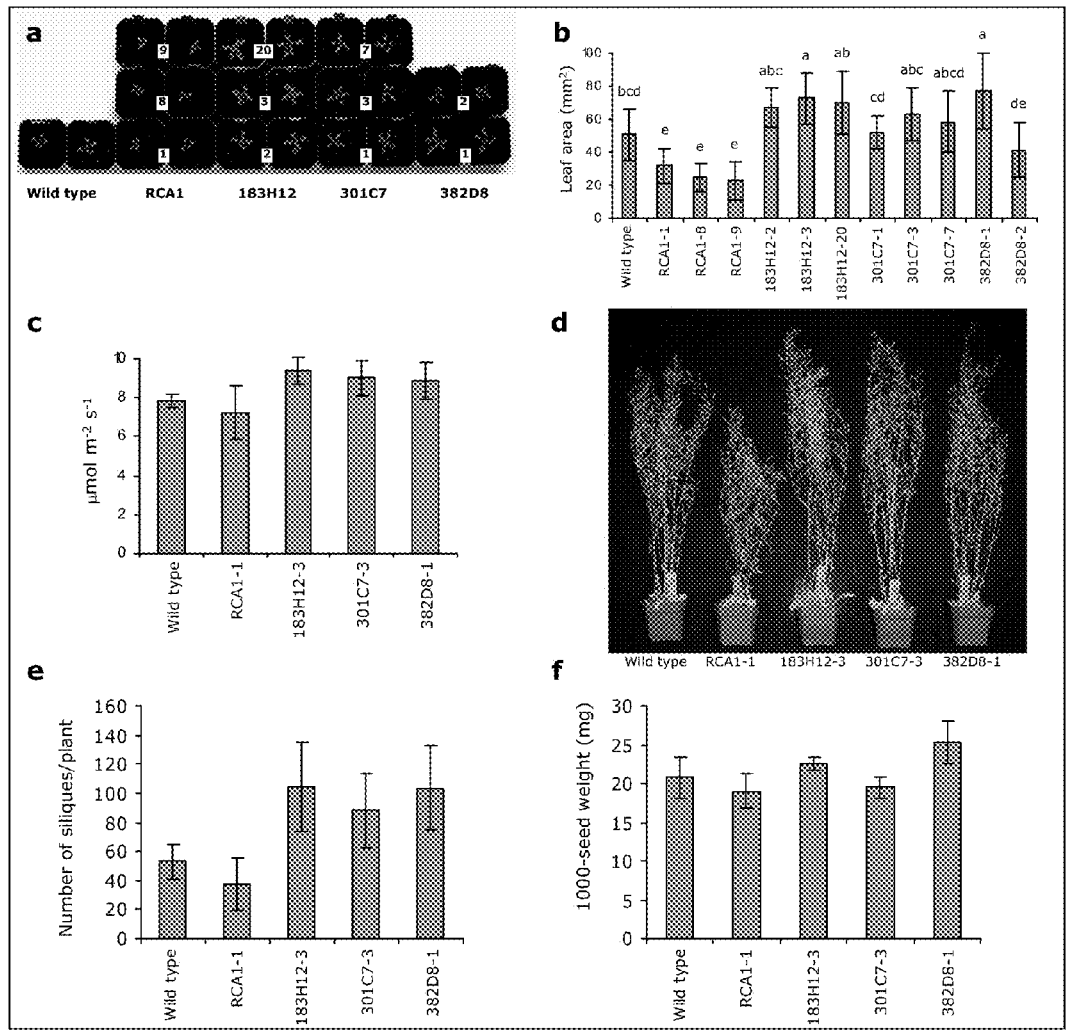
FIGS. 5A-5F: Effect of moderate heat stress (30° C. for 4 hr per day) on wild type plants and Δrca mutants expressing RCA1 or thermostable variants 183H12, 301C7 and 382D8. (A) Photograph of the plants showing differential growth rates mediated by the RCA variant. (B) Leaf area of 8-10 independent plants per line, analyzed using a fluorescence image analysis system. Means followed by common letters are not significantly different at P=0.05 using a protected LSD. (C) Net photosynthesis of four independent plants from selected lines, monitored by gas exchange analysis after 2 hr at 30° C. (D) Photograph of mature plants (8-weeks old) described in (C). (E) Number of siliques per plant. Eight to ten independent plants per line were analyzed. (F) Seed weight/1000 seeds of seeds harvested from the selected lines (5 independent plants per line).

Since exposure of Arabidopsis plants to 30° C. causes minor induction of heat shock proteins (typically induced at 32° C. and above) and minor effects on stomatal aperture (Salvucci, et al., (2001) Plant Physiol. 127:1053-1064), growth under prolonged heat treatment was conducted with Arabidopsis plants expressing wild type or thermostable Rubisco Activase. Four-week old transgenic lines exposed for two weeks to moderate heat stress. Conditions of growth were 16 hours of light at 225 µmol photons m$^{-2}$ s$^{-1}$ and 8 hours of dark. During the light cycle, plants were grown at 22° C. for 6 hours then rapidly increased to 30° C. (2° C. per min) for 4 hours and then returned to 22° C. for the completion of the light cycle. During the dark cycle, plants remained at 22° C. Characterization of growth, biomass, and yield was performed as previously described (Barth, et al., (2003) *Heredity.* 91:36-42). The plants displayed normal phenotype and leaf color but varied in size (FIG. 5A). ΔrcaRCA1 (lines 1, 8 and 9) were stunted by comparison to wild-type untransformed plants and to the Δrca lines that express the Rubisco Activase derived polypeptides (FIG. 5B). Transgenic *Arabidopsis* expressing 183H12-3 that possesses the highest in vitro specific activity were the largest plants. Lines that expressed 301C7 and 382D8 were larger than ΔrcaRCA1 lines but did not reach the leaf area levels of the 183H12 lines. While Δrca lines expressing only the short form of the wild-type gene (RCA1) were smaller than wild-type untransformed lines (expressing both short and long forms), most transgenic lines expressing the Rubisco Activase derived polypeptides exhibited greater leaf area than wild-type untransformed plants (FIG. 5B), and all lines expressing the Rubisco Activase derived polypeptides were significantly larger (P=0.01) than the Δrca transformants expressing RCA1.

Four-week old plants exposed to two weeks of moderate heat stress also showed differences in rates of plant development. At the end of the treatment period 74, 44 and 33% of Δrca183H12, Δrca301C7 and Δrca382D8, respectively, had mature inflorescences with open flowers, while 100% of untransformed wild-type plants and 88% of ΔrcaRCA1 lines had emerging immature inflorescences with no open flowers (data not shown). Additionally, 12% of the ΔrcaRCA1 lines were in the vegetative stage with no visible inflorescences. Under normal growth conditions, *Arabidopsis* plants flower after four weeks. Therefore, the relatively high percentage of Δrca183H12, Δrca301C7 and Δrca382D8 lines showing normal development is likely due to improved thermostability of RCA that minimized the inhibition of photosynthesis and growth under moderate heat stress conditions.

The best line from each variant was further analyzed for photosynthetic activity during the moderate heat stress cycle (after 2 hr at 30° C.). Transgenic lines showed a $CO_2$ fixation pattern that correlated with leaf area. Rates of $CO_2$ fixation in lines Δrca183H12-3, Δrca301C7-3 and Δrca382D8-1 were 30, 25 and 23% higher, respectively, than in line ΔrcaRCA1-1. These results demonstrated that Rubisco activase is a limiting factor in photosynthesis under the experimental conditions.

Mature plants (10 weeks old) exposed for 8 weeks to moderate heat stress were similar in appearance. A slight positive effect on plant height was detected in Δrca183H12-3, Δrca301C7-3 and Δrca382D8-1 lines (116, 121 and 119% respectively) compared to ΔrcaRCA1-1 (FIG. 5D). A dramatic difference was observed in the number of siliques per plant, which was 130.8±48.2, 84.3±19.6 and 100.8±26.9 for Δrca183H12-3, Δrca301C7-3 and Δrca382D8-1 (respectively) compared to 40.2±16.3 and 47.5±15.8 for ΔrcaRCA1-1 and wild-type, respectively (FIG. 5E).

To confirm that the relatively enhanced formation of siliques in transformants expressing improved RCA was not at the expense of individual seed size, the weights of lots of 1000 seeds were compared. As shown in FIG. 5F, Δrca183H12-3, and Δrca382D8-1 produced slightly larger seeds (18 and 32% respectively) than ΔrcaRCA1-1, while the seed weight of Δrca301C7-3 and wild-type plants was similar to that of ΔrcaRCA1-1.

Figure 6:
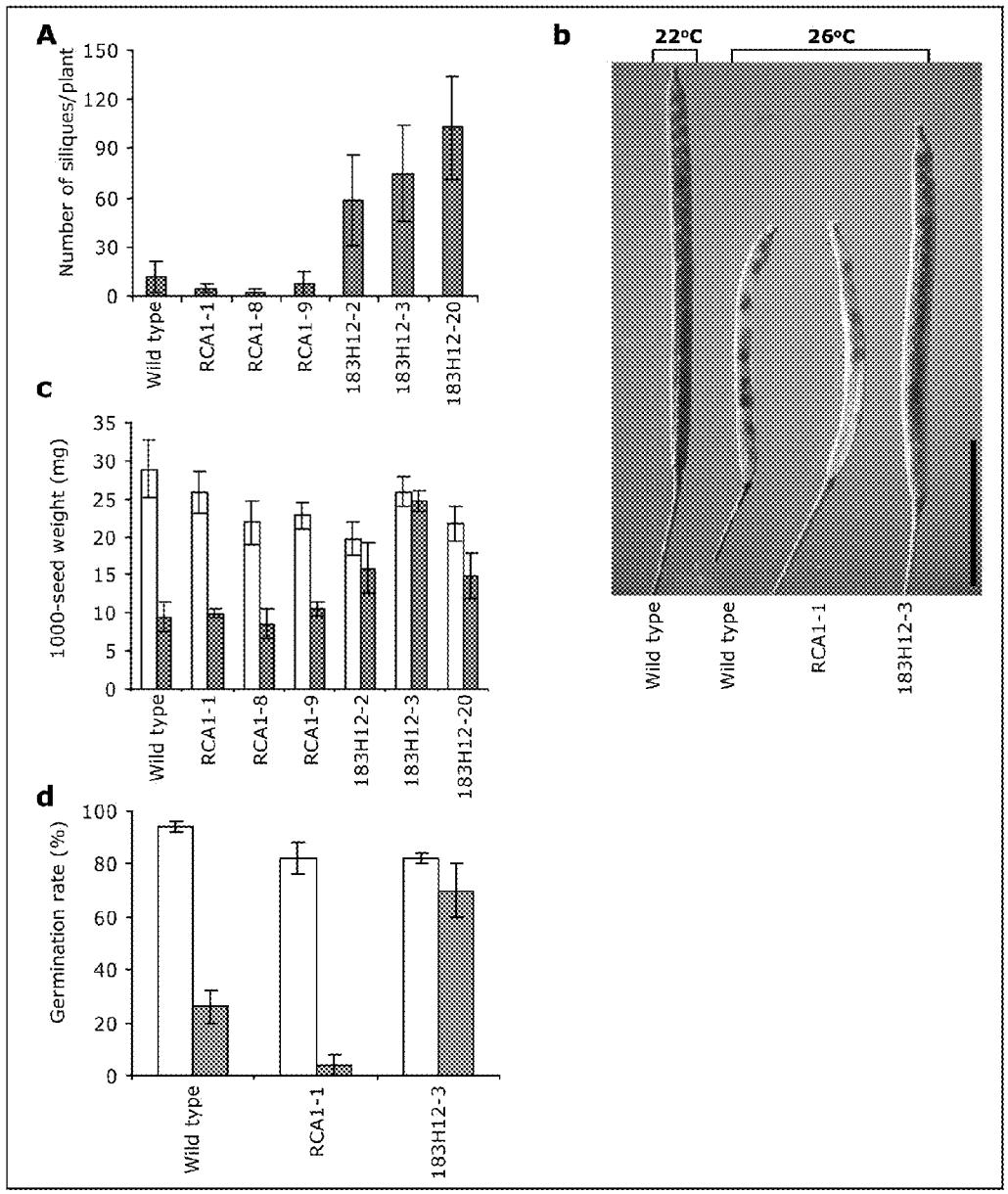
FIGS. 6A-6D: Effect of 26° C. heat stress on development and yield of wild type plants and Δrca mutant lines expressing RCA1 and thermostable variant 183H12. (A) Number of siliques per plant. Ten to twelve independent plants per line were analyzed. (B) Photograph of siliques from selected lines grown at the indicated temperature showing variation in siliqe size and seed set. Bar=0.5 cm. (C) Seed weight/1000 seeds for seeds harvested from the plants described in (A). (D) Germination rates (at 22° C.) of seeds (250 seeds per line) harvested from *Arabidopsis* plants that were grown at 22° C. (white) or 26° C. (gray).

To further analyze the effect of improved RCA on growth under moderate temperature stress, T3 lines expressing the most active clone at 25° C. (in vitro), 183H12, were grown continuously at 26° C. under higher light intensity and humidity than in the previous experiment. Conditions of growth were 16 hours of light at 300 µmol photons m$^{-2}$ s$^{-1}$ and 8 hours of dark at 26° C. and 85% humidity. Wild-type and ΔrcaRCA1 lines grown at 26° C. produced slightly decreased overall biomass and exhibited slow rates of plant development than under normal growth conditions, whereas the biomass and the developmental process of lines of Δrca183H12 was unchanged (not shown). In contrast, the number of siliques per plant produced by Δrca plants grown at 26° C. was dramatically affected by the Rubisco Activase derived polypeptide they expressed (FIG. 6A). Δrca183H12 lines possessed 50 to 100 more siliques per plant than ΔrcaRCA1 lines and 40 to 80 more siliques per plant than wild-type plants. In addition, the siliques of Δrca183H12 were larger than those of wild-type plants and the ΔrcaRCA1 lines and produced more seeds (FIG. 6B). Siliques from Δrca183H12 at 26° C. exhibited a similar phenotype to the wild-type grown under normal growth conditions, but produced fewer seeds. Under normal growth conditions a minor decrease in seed weight was observed in Δrca lines expressing RCA1 and 183H12 compared to wild-type plants (FIG. 6C; white bars). However, under continuous exposure to 26° C., 50% to 150% greater seed weight was observed in lines of Δrca183H12 than in either wild-type plants or lines of ΔrcaRCA1. In comparing seed weight for each line grown at 26° C. to that of the same line grown at 22° C., lines Δrca183H12-2, Δrca183H12-3 and Δrca183H12-20 were strikingly less affected by the higher growth temperature than the ΔrcaRCA1 lines or the wild type.

Since exposure to 26° C. resulted in small siliques containing few seeds of small seed-weight, seed viability was analyzed using a germination test. Seeds from wild-type, ΔrcaRCA1-1 and Δrca183H12-3 were collected from plants grown at normal growth conditions and 26° C. and then germinated at 22° C. Seeds from ΔrcaRCA1-1 and Δrca183H12-3 lines of parents grown at 22° C., showed the same germination rate (86%), which was slightly lower than that of wild-type plants (94%) (FIG. 6C). Complete inhibition of germination (4%) was observed in ΔrcaRCA1-1 seeds collected from parents grown at 26° C. and significant inhibition in wild-type seeds (26%). Conversely, Δrca183H12-3 seeds collected from parents grown at 26° C. exhibited relatively high germination rates of 70%.

Additionally plants were analyzed for photosynthesis rates, growth rates and seed yield under the following growth conditions:

Normal:

Plants were grown under 16 hours light (225 µmol photons m$^{-2}$ s$^{-1}$) and 8 hour dark regime at 22° C.

Increased Temperatures:

Plants were grown under normal growth conditions for two weeks and then transferred to the growth chamber and grown under 16 hour light (225 µmol photons m$^{-2}$ s$^{-1}$) and 8 hour dark regime. During the light cycle, the temperature was set to 22° C. for six hours and then rapidly increased to 30° C. (2° C. per minute) for four hours. After the heat treatment, the temperature was set back to 22° C.

Continuous Increased Temperatures:

Plants were grown under normal growth conditions for two weeks and then transferred to the growth room and grown under sixteen hours high light (300 µmol photons m$^{-2}$ s$^{-1}$) and eight hour dark regime. During the light/dark cycle the temperature was set to 26° C. and the humidity to 80%.

The results of the in planta assays of Rubisco Activase derived polypeptide activity at the conditions identified supra are summarized below.

Growth Rates.

Leaf area was measured using the chlorophyll a fluorescence imaging system (FluorImager, Qubit System Inc.). Leaf area observed in untransformed wild type plants under the different growth conditions was set to 100%. The data in Table 4 demonstrates that plants expressing any of the three Rubisco Activase derived polypeptides had increased growth rates under increased temperatures as compared to either wild type plants or plants expressing a transgenic wild type Rubisco Activase.

Photosynthesis Rates.

Plants were analyzed for $CO_2$ fixation using the portable infrared gas analyzer (LI6400, Li-Cor) for 15 minutes. The light source was set to 225 µmol photons $m^{-2} s^{-1}$ and the level of $CO_2$ supplied to the leaf by the built-in $CO_2$ injection system was 350 µmol $m^{-2}s^{-1}$. The data in Table 5 shows that plants expressing any of the three Rubisco Activase derived polypeptides had increased photosynthetic rates under increased temperatures as compared to either wild type plants or plants expressing a transgenic wild type Rubisco Activase (see, column 3).

Seed Yield.

Seed weight (mg) was determined from mature dried plants. Seed germination rate was determined by number of plants germinated on MS plate supplemented with Kanamycin. The data in Table 5 shows that plants expressing any of the three Rubisco Activase derived polypeptides had increased seed yield under increased temperatures as compared to either wild type plants or plants expressing a transgenic wild type Rubisco Activase (see, column 4). The increased seed yield was also present in plants expressing any of the three Rubisco Activase derived polypeptides under continuous increased temperature conditions (see, Table 6). Germination rates of seeds was increased under continuous increased temperature conditions in plants expressing the Rubisco Activase derived polypeptide 183H12 (SEQ ID NO: 7) as compared to either wild type plants or plants expressing a transgenic wild type Rubisco Activase (see, Table 7).

TABLE 1

Codon Table

| Amino acid | | | Codon |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

TABLE 2

Effect of amino acids substitution on Rubisco Activase activity and thermostability.

| | Amino acid position | | | | | | | | Activity ($3^{rd}$ tier) µmol $CO_2$ $min^{-1}$ $mg^{-1}$ | | Thermo-stability* |
|---|---|---|---|---|---|---|---|---|---|---|---|
| Clone | 42 | 130 | 131 | 168 | 257 | 274 | 293 | 310 | 25° C. | 40° C. | (%) |
| Wild type (SEQ ID NO: 1) | M | M | M | F | V | T | R | K | 0.96 ± 0.04 | 0.634 ± 0.02 | 66 |
| 126H4 (SEQ ID NO: 3) | | R | | | | | | | 0.616 ± 0.04 | 0.596 ± 0.05 | 97 |
| 182B11 (SEQ ID NO: 5) | | | I | | | | | | 0.426 ± 0.03 | 0.359 ± 0.01 | 84 |
| 183H12 (SEQ ID NO: 7) | | | | | | | R | | 1.049 ± 0.02 | 0.857 ± 0.01 | 82 |
| 184B2 (SEQ ID NO: 9) | | | | | | | | N | 1.055 ± 0.03 | 0.889 ± 0.02 | 84 |
| 079H6 (SEQ ID NO: 11) | T | | I | | | | K | | 1.064 ± 0.01 | 0.940 ± 0.02 | 88 |
| 214A4 (SEQ ID NO: 13) | T | | | | | | R | | 1.069 ± 0.06 | 0.986 ± 0.04 | 92 |

TABLE 2-continued

Effect of amino acids substitution on Rubisco Activase activity and thermostability.

| | Amino acid position | | | | | | | | Activity (3$^{rd}$ tier) μmol $CO_2$ min$^{-1}$ mg$^{-1}$ | | Thermo-stability* |
|---|---|---|---|---|---|---|---|---|---|---|---|
| Clone | 42 | 130 | 131 | 168 | 257 | 274 | 293 | 310 | 25° C. | 40° C. | (%) |
| 382D8 (SEQ ID NO: 15) | | V | | I | | | | N | 1.012 ± 0.05 | 0.91 ± 0.06 | 90 |
| 383A12 (SEQ ID NO: 17) | | | L | I | | R | | N | 0.891 ± 0.02 | 0.920 ± 0.02 | 103 |
| 301C7 (SEQ ID NO: 19) | | | L | I | | | | N | 0.905 ± 0.04 | 0.889 ± 0.01 | 98 |
| 301H3 (SEQ ID NO: 21) | | | | I | | R | | N | 0.971 ± 0.05 | 0.860 ± 0.05 | 89 |

*Percent of activated Rubisco at 40° C. compared to amount of activated Rubisco 25° C.

TABLE 3

Relative activity (%) of Rubisco Activase Derived Polypeptides.

| | Activation of deactivated Rubisco assay | | | Rubisco activation under catalytic conditions assay | | ATPase assay | |
|---|---|---|---|---|---|---|---|
| Clone | 25° C. | T.S 45° C./ 25° C. | T.S 45 min at 40° C./15 min at 25° C. | 25° C. | T.S 40° C./ 25° C. | 25° C. | T.S 40° C./ 25° C. |
| Wild type (SEQ ID NO: 1) | 100 | 50 | 32 | 100 | 67 | 100 | 8 |
| 183H12 (SEQ ID NO: 7) | 109 | 52 | 54 | 118 | 77 | 123 | 28 |
| 079H6 (SEQ ID NO: 11) | 111 | 63 | 66 | 105 | 82 | 119 | 72 |
| 214A4 (SEQ ID NO: 13) | 111 | 58 | 65 | 101 | 74 | 124 | 38 |
| 382D8 (SEQ ID NO: 15) | 105 | 86 | 85 | 98 | 93 | 112 | 113 |
| 383A12 (SEQ ID NO: 17) | 93 | 92 | 88 | 96 | 97 | 93 | 92 |
| 301C7 (SEQ ID NO: 19) | 94 | 84 | 92 | 96 | 83 | 105 | 89 |
| 301H3 (SEQ ID NO: 21) | 101 | 89 | 75 | 92 | 78 | 107 | 112 |

TABLE 4

Leaf area under normal and increased temperature conditions.

| | | Leaf area (%)* | |
|---|---|---|---|
| Clone | Line ID | Normal growth conditions | Increased Temperatures |
| Wild type | Untransformed | 100 ± 13 | 100 ± 30 |
| Wild type | RCA1-1 | 92 ± 26 | 62 ± 21 |
| (SEQ ID NO: 1) | RCA1-8 | 106 ± 30 | 48 ± 16 |
| | RCA1-9 | 88 ± 27 | 45 ± 23 |
| 183H12 | 183H12-2 | 110 ± 25 | 131 ± 23 |
| (SEQ ID NO: 7) | 183H12-3 | 113 ± 17 | 142 ± 31 |
| | 183H12-20 | 101 ± 30 | 138 ± 37 |
| 382D8 | 382D8-1 | 126 ± 23 | 151 ± 46 |
| (SEQ ID NO: 15) | 382D8-2 | 90 ± 31 | 81 ± 32 |
| 301C7 | 301C7-1 | 105 ± 30 | 101 ± 19 |

TABLE 4-continued

Leaf area under normal and increased temperature conditions.

| | | Leaf area (%)* | |
|---|---|---|---|
| Clone | Line ID | Normal growth conditions | Increased Temperatures |
| (SEQ ID NO: 19) | 301C7-3 | 104 ± 30 | 124 ± 31 |
| | 301C7-7 | 116 ± 23 | 115 ± 36 |

*The leaf area of the *Arabidopsis* wild-type untransformed was set to 100%.

TABLE 5

Photosynthesis rates and seed yield under normal and increased temperature conditions.

| Clone | Line ID | Photosynthesis* ($\mu mol\ CO_2\ m^{-2}\ s^{-1}$) | Seed yield# (%) |
|---|---|---|---|
| Wild type | Untransformed | 7.85 ± 0.36 | 72 ± 14 |
| Wild type (SEQ ID NO: 1) | RCA1-1 | 7.25 ± 1.36 | 74 ± 12 |
| 183H12 (SEQ ID NO: 7) | 183H12-3 | 9.41 ± 0.66 | 87 ± 8 |
| 382D8 (SEQ ID NO: 15) | 382D8-1 | 8.9 ± 0.93 | 100 ± 11 |
| 301C7 (SEQ ID NO: 19) | 301C7-3 | 9.03 ± 0.9 | 87 ± 16 |

*Net photosynthesis was monitored after 2 hours at 30° C.
Percent of weight of 1000 seeds from plants grown under increased temperatures as compared to weight of 1000 seeds from plants grown under normal conditions.

TABLE 6

Seed yield under normal and continuous increased temperature conditions.

| | | 1000-seed weight (mg) | |
|---|---|---|---|
| Clone | Line ID | Normal growth conditions | Continuous increased temperatures |
| Wild type | Untransformed | 28.900 ± 4.140 | 9.484 ± 1.971 |
| Wild type (SEQ ID NO: 1) | RCA1-1 | 25.837 ± 2.721 | 8.501 ± 1.921 |
| | RCA1-8 | 21.880 ± 2.839 | 10.529 ± 0.830 |
| | RCA1-9 | 22.846 ± 1.714 | 9.861 ± 0.596 |
| 183H12 (SEQ ID NO: 7) | 183H12-2 | 19.773 ± 2.112 | 15.858 ± 3.249 |
| | 183H12-3 | 25.934 ± 1.869 | 24.812 ± 1.376 |
| | 183H12-20 | 21.730 ± 2.284 | 14.955 ± 2.996 |

TABLE 7

Germination rates of seeds harvested from plants grown under normal and continuous increased temperature conditions.

| | | Germinated seeds (%) | |
|---|---|---|---|
| Clone | Line ID | Normal growth conditions | Continuous increased temperatures |
| Wild type | Untransformed | 94 ± 2 | 26 ± 6 |
| Wild type (SEQ ID NO: 1) | RCA1-1 | 82 ± 6 | 4 ± 4 |
| 183H12 (SEQ ID NO: 7) | 183H12-3 | 82 ± 2 | 70 ± 10 |

What is claimed is:

1. A transgenic plant comprising a transgene that expresses
   a. the polypeptide of SEQ ID NO: 18, or
   b. the nucleic acid molecule of SEQ ID NO: 17.

2. The transgenic plant of claim 1, wherein the plant is selected from the group consisting of maize, tomato, potato, rice, soybean, cotton, sunflower, alfalfa, lettuce, canola, sorghum or tobacco plants.

3. The transgenic plant of claim 1, wherein the transgenic plant has increased heat tolerance as compared to a plant that is not transgenic.

* * * * *

SEQUENCE LISTING

<160> NUMBER OF SEQ ID NOS: 26

<210> SEQ ID NO 1
<211> LENGTH: 1173
<212> TYPE: DNA
<213> ORGANISM: Arabidopsis thaliana

<400> SEQUENCE: 1

```
atggtgaaag aagacaaaca aaccgatgga gacagatgga gaggtcttgc ctacgacact    60
tctgatgatc aacaagacat caccagaggc aagggtatgg ttgactctgt cttccaagct   120
cctatgggaa ccggaactca ccacgctgtc cttagctcat acgaatacgt tagccaaggc   180
cttaggcagt acaacttgga acacatgatg gatgggtttt acattgctcc tgctttcatg   240
gacaagcttg ttgttcacat caccaagaac ttcttgactc tgcctaacat caaggttcca   300
cttattttgg gtatatgggg aggcaaaggt caaggtaaat ccttccagtg tgagcttgtc   360
atggccaaga tgggtatcaa cccaatcatg atgagtgctg agagcttga gagtggaaac   420 gcaggagaac ccgcaaagct tatccgtcag aggtaccgtg aggcagctga cttgatcaag   480
aagggaaaga tgtgttgtct cttcatcaac gatcttgacg ctggtgcggg tcgtatgggt   540
ggtactactc agtacactgt caacaaccag atggttaacg caacactcat gaacattgct   600
gataacccaa ccaacgtcca gctcccagga atgtacaaca aggaagagaa cgcacgtgtc   660
cccatcattt gcactggtaa cgatttctcc accctatacg ctcctctcat ccgtgatgga   720
cgtatggaga agttctactg ggccccgacc cgtgaagacc gtatcggtgt ctgcaagggt   780
atcttcagaa ctgacaagat caaggacgaa gacattgtca cacttgttga tcagttccct   840
```

```
ggtcaatcta tcgatttctt cggtgctttg agggcgagag tgtacgatga tgaagtgagg    900
aagttcgttg agagccttgg agttgagaag atcggaaaga ggctggttaa ctcaagggaa    960
ggacctcccg tgttcgagca acccgagatg acttatgaga agcttatgga atacggaaac   1020
atgcttgtga tggaacaaga gaatgtcaag agagtccaac ttgccgagac ctacctcagc   1080
caggctgctt tgggagacgc aaacgctgac gccatcggcc gcggaacttt ctacggtaaa   1140
acagaggaaa aggagcccag caagctcgag taa                                1173
```

<210> SEQ ID NO 2
<211> LENGTH: 390
<212> TYPE: PRT
<213> ORGANISM: Arabidopsis thaliana

<400> SEQUENCE: 2

```
Met Val Lys Glu Asp Lys Gln Thr Asp Gly Asp Arg Trp Arg Gly Leu
  1               5                  10                  15

Ala Tyr Asp Thr Ser Asp Asp Gln Gln Asp Ile Thr Arg Gly Lys Gly
                 20                  25                  30

Met Val Asp Ser Val Phe Gln Ala Pro Met Gly Thr Gly Thr His His
             35                  40                  45

Ala Val Leu Ser Ser Tyr Glu Tyr Val Ser Gln Gly Leu Arg Gln Tyr
         50                  55                  60

Asn Leu Asp Asn Met Met Asp Gly Phe Tyr Ile Ala Pro Ala Phe Met
 65                  70                  75                  80

Asp Lys Leu Val Val His Ile Thr Lys Asn Phe Leu Thr Leu Pro Asn
                 85                  90                  95

Ile Lys Val Pro Leu Ile Leu Gly Ile Trp Gly Gly Lys Gly Gln Gly
            100                 105                 110

Lys Ser Phe Gln Cys Glu Leu Val Met Ala Lys Met Gly Ile Asn Pro
        115                 120                 125

Ile Met Met Ser Ala Gly Glu Leu Glu Ser Gly Asn Ala Gly Glu Pro
    130                 135                 140

Ala Lys Leu Ile Arg Gln Arg Tyr Arg Glu Ala Ala Asp Leu Ile Lys
145                 150                 155                 160

Lys Gly Lys Met Cys Cys Leu Phe Ile Asn Asp Leu Asp Ala Gly Ala
                165                 170                 175

Gly Arg Met Gly Gly Thr Thr Gln Tyr Thr Val Asn Asn Gln Met Val
            180                 185                 190

Asn Ala Thr Leu Met Asn Ile Ala Asp Asn Pro Thr Asn Val Gln Leu
        195                 200                 205

Pro Gly Met Tyr Asn Lys Glu Glu Asn Ala Arg Val Pro Ile Ile Cys
    210                 215                 220

Thr Gly Asn Asp Phe Ser Thr Leu Tyr Ala Pro Leu Ile Arg Asp Gly
225                 230                 235                 240

Arg Met Glu Lys Phe Tyr Trp Ala Pro Thr Arg Glu Asp Arg Ile Gly
                245                 250                 255

Val Cys Lys Gly Ile Phe Arg Thr Asp Lys Ile Lys Asp Glu Asp Ile
            260                 265                 270

Val Thr Leu Val Asp Gln Phe Pro Gly Gln Ser Ile Asp Phe Phe Gly
        275                 280                 285

Ala Leu Arg Ala Arg Val Tyr Asp Asp Glu Val Arg Lys Phe Val Glu
    290                 295                 300

Ser Leu Gly Val Glu Lys Ile Gly Lys Arg Leu Val Asn Ser Arg Glu
305                 310                 315                 320
```

Gly Pro Pro Val Phe Glu Gln Pro Glu Met Thr Tyr Glu Lys Leu Met
                325                 330                 335

Glu Tyr Gly Asn Met Leu Val Met Gln Glu Asn Val Lys Arg Val
            340                 345                 350

Gln Leu Ala Glu Thr Tyr Leu Ser Gln Ala Ala Leu Gly Asp Ala Asn
        355                 360                 365

Ala Asp Ala Ile Gly Arg Gly Thr Phe Tyr Lys Thr Glu Glu Lys
    370                 375                 380

Glu Pro Ser Lys Leu Glu
385                 390

<210> SEQ ID NO 3
<211> LENGTH: 1173
<212> TYPE: DNA
<213> ORGANISM: Artificial Sequence
<220> FEATURE:
<223> OTHER INFORMATION: Based on Arabidopsis thaliana sequence

<400> SEQUENCE: 3

```
atggtgaaag aagacaaaca aaccgatgga gacagatgga gaggtcttgc ctacgacact      60
tctgatgatc aacaagacat caccagaggc aagggtatgg ttgactctgt cttccaagct     120
cctatgggaa ccggaactca ccacgctgtc cttagctcat acgaatacgt tagccaaggc     180
cttaggcagt acaacttgga caacatgatg gatgggtttt acattgctcc tgctttcatg     240
gacaagcttg ttgttcacat caccaagaac ttcttgactc tgcctaacat caaggttcca     300
cttattttgg gtatatgggg aggcaaaggt caaggtaaat ccttccagtg tgagcttgtc     360
atggccaaga tgggtatcaa cccaatcagg atgagtgctg agagcttga gagtggaaac      420 gcaggagaac ccgcaaagct tatccgtcag aggtaccgtg aggcagctga cttgatcaag     480
aagggaaaga tgtgttgtct cttcatcaac gatcttgacg ctggtgcggg tcgtatgggt     540
ggtactactc agtacactgt caacaaccag atggttaacg caacactcat gaacattgct     600
gataacccaa ccaacgtcca gctcccagga atgtacaaca aggaagagaa cgcacgtgtc     660
cccatcattt gcactggtaa cgatttctcc accctatacg ctcctctcat ccgtgatgga     720
cgtatggaga agttctactg ggccccgacc cgtgaagacc gtatcggtgt ctgcaagggt     780
atcttcagaa ctgacaagat caaggacgaa gacattgtca cacttgttga tcagttccct     840
ggtcaatcta tcgatttctt cggtgctttg agggcgagag tgtacgatga tgaagtgagg     900
aagttcgttg agagccttgg agttgagaag atcggaaaga ggctggttaa ctcaagggaa     960
ggacctcccg tgttcgagca acccgagatg acttatgaga agcttatgga atacggaaac    1020
atgcttgtga tggaacaaga aatgtcaag agagtccaac ttgccgagac ctacctcagc    1080
caggctgctt tgggagacgc aaacgctgac gccatcggcc gcggaacttt ctacggtaaa    1140
acagaggaaa aggagcccag caagctcgag taa                                 1173
```

<210> SEQ ID NO 4
<211> LENGTH: 390
<212> TYPE: PRT
<213> ORGANISM: Artificial Sequence
<220> FEATURE:
<223> OTHER INFORMATION: Based on Arabidopsis thaliana sequence

<400> SEQUENCE: 4

Met Val Lys Glu Asp Lys Gln Thr Asp Gly Asp Arg Trp Arg Gly Leu
1               5                   10                  15

Ala Tyr Asp Thr Ser Asp Asp Gln Gln Asp Ile Thr Arg Gly Lys Gly

```
                20                  25                  30
Met Val Asp Ser Val Phe Gln Ala Pro Met Gly Thr Gly Thr His His
         35                  40                  45

Ala Val Leu Ser Ser Tyr Glu Tyr Val Ser Gln Gly Leu Arg Gln Tyr
 50                  55                  60

Asn Leu Asp Asn Met Met Asp Gly Phe Tyr Ile Ala Pro Ala Phe Met
 65                  70                  75                  80

Asp Lys Leu Val Val His Ile Thr Lys Asn Phe Leu Thr Leu Pro Asn
                 85                  90                  95

Ile Lys Val Pro Leu Ile Leu Gly Ile Trp Gly Gly Lys Gly Gln Gly
            100                 105                 110

Lys Ser Phe Gln Cys Glu Leu Val Met Ala Lys Met Gly Ile Asn Pro
        115                 120                 125

Ile Arg Met Ser Ala Gly Glu Leu Glu Ser Gly Asn Ala Gly Glu Pro
    130                 135                 140

Ala Lys Leu Ile Arg Gln Arg Tyr Arg Glu Ala Ala Asp Leu Ile Lys
145                 150                 155                 160

Lys Gly Lys Met Cys Cys Leu Phe Ile Asn Asp Leu Asp Ala Gly Ala
                165                 170                 175

Gly Arg Met Gly Gly Thr Thr Gln Tyr Thr Val Asn Asn Gln Met Val
            180                 185                 190

Asn Ala Thr Leu Met Asn Ile Ala Asp Asn Pro Thr Asn Val Gln Leu
        195                 200                 205

Pro Gly Met Tyr Asn Lys Glu Glu Asn Ala Arg Val Pro Ile Ile Cys
    210                 215                 220

Thr Gly Asn Asp Phe Ser Thr Leu Tyr Ala Pro Leu Ile Arg Asp Gly
225                 230                 235                 240

Arg Met Glu Lys Phe Tyr Trp Ala Pro Thr Arg Glu Asp Arg Ile Gly
                245                 250                 255

Val Cys Lys Gly Ile Phe Arg Thr Asp Lys Ile Lys Asp Glu Asp Ile
            260                 265                 270

Val Thr Leu Val Asp Gln Phe Pro Gly Gln Ser Ile Asp Phe Phe Gly
        275                 280                 285

Ala Leu Arg Ala Arg Val Tyr Asp Asp Glu Val Arg Lys Phe Val Glu
    290                 295                 300

Ser Leu Gly Val Glu Lys Ile Gly Lys Arg Leu Val Asn Ser Arg Glu
305                 310                 315                 320

Gly Pro Pro Val Phe Glu Gln Pro Glu Met Thr Tyr Glu Lys Leu Met
                325                 330                 335

Glu Tyr Gly Asn Met Leu Val Met Glu Gln Glu Asn Val Lys Arg Val
            340                 345                 350

Gln Leu Ala Glu Thr Tyr Leu Ser Gln Ala Ala Leu Gly Asp Ala Asn
        355                 360                 365

Ala Asp Ala Ile Gly Arg Gly Thr Phe Tyr Gly Lys Thr Glu Glu Lys
    370                 375                 380

Glu Pro Ser Lys Leu Glu
385                 390

<210> SEQ ID NO 5
<211> LENGTH: 1173
<212> TYPE: DNA
<213> ORGANISM: Artificial Sequence
<220> FEATURE:
<223> OTHER INFORMATION: Based on Arabidopsis thaliana sequence

<400> SEQUENCE: 5
```

```
atggtgaaag aagacaaaca aaccgatgga gacagatgga gaggtcttgc ctacgacact    60
tctgatgatc aacaagacat caccagaggc aagggtatgg ttgactctgt cttccaagct   120
cctatgggaa ccggaactca ccacgctgtc cttagctcat acgaatacgt tagccaaggc   180
cttaggcagt acaacttgga caacatgatg gatgggtttt acattgctcc tgctttcatg   240
gacaagcttg ttgttcacat caccaagaac ttcttgactc tgcctaacat caaggttcca   300
cttattttgg gtatatgggg aggcaaaggt caaggtaaat ccttccagtg tgagcttgtc   360
atggccaaga tgggtatcaa cccaatcatg ataagtgctg gagagcttga gagtggaaac   420
gcaggagaac ccgcaaagct tatccgtcag aggtaccgtg aggcagctga cttgatcaag   480
aagggaaaga tgtgttgtct cttcatcaac gatcttgacg ctggtgcggg tcgtatgggt   540
ggtactactc agtacactgt caacaaccag atggttaacg caacactcat gaacattgct   600
gataacccaa ccaacgtcca gctcccagga atgtacaaca aggaagagaa cgcacgtgtc   660
cccatcattt gcactggtaa cgatttctcc accctatacg ctcctctcat ccgtgatgga   720
cgtatggaga agttctactg gccccgacc cgtgaagacc gtatcggtgt ctgcaagggt   780
atcttcagaa ctgacaagat caaggacgaa gacattgtca cacttgttga tcagttccct   840
ggtcaatcta tcgatttctt cggtgctttg agggcgagag tgtacgatga tgaagtgagg   900
aagttcgttg agagccttgg agttgagaag atcggaaaga ggctggttaa ctcaagggaa   960
ggacctcccg tgttcgagca acccgagatg acttatgaga agcttatgga atacggaaac  1020
atgcttgtga tggaacaaga gaatgtcaag agagtccaac ttgccgagac ctacctcagc  1080
caggctgctt tgggagacgc aaacgctgac gccatcggcc gcggaacttt ctacggtaaa  1140
acagaggaaa aggagcccag caagctcgag taa                                1173
```

<210> SEQ ID NO 6  
<211> LENGTH: 390  
<212> TYPE: PRT  
<213> ORGANISM: Artificial Sequence  
<220> FEATURE:  
<223> OTHER INFORMATION: Based on Arabidopsis thaliana sequence

<400> SEQUENCE: 6

```
Met Val Lys Glu Asp Lys Gln Thr Asp Gly Asp Arg Trp Arg Gly Leu
  1               5                  10                  15

Ala Tyr Asp Thr Ser Asp Asp Gln Gln Asp Ile Thr Arg Gly Lys Gly
             20                  25                  30

Met Val Asp Ser Val Phe Gln Ala Pro Met Gly Thr Gly Thr His His
         35                  40                  45

Ala Val Leu Ser Ser Tyr Glu Tyr Val Ser Gln Gly Leu Arg Gln Tyr
     50                  55                  60

Asn Leu Asp Asn Met Met Asp Gly Phe Tyr Ile Ala Pro Ala Phe Met
 65                  70                  75                  80

Asp Lys Leu Val Val His Ile Thr Lys Asn Phe Leu Thr Leu Pro Asn
                 85                  90                  95

Ile Lys Val Pro Leu Ile Leu Gly Ile Trp Gly Gly Lys Gly Gln Gly
            100                 105                 110

Lys Ser Phe Gln Cys Glu Leu Val Met Ala Lys Met Gly Ile Asn Pro
        115                 120                 125

Ile Met Ile Ser Ala Gly Glu Leu Glu Ser Gly Asn Ala Gly Glu Pro
    130                 135                 140

Ala Lys Leu Ile Arg Gln Arg Tyr Arg Glu Ala Ala Asp Leu Ile Lys
145                 150                 155                 160
```

```
Lys Gly Lys Met Cys Cys Leu Phe Ile Asn Asp Leu Asp Ala Gly Ala
            165                 170                 175
Gly Arg Met Gly Gly Thr Thr Gln Tyr Thr Val Asn Asn Gln Met Val
        180                 185                 190
Asn Ala Thr Leu Met Asn Ile Ala Asp Asn Pro Thr Asn Val Gln Leu
            195                 200                 205
Pro Gly Met Tyr Asn Lys Glu Glu Asn Ala Arg Val Pro Ile Ile Cys
    210                 215                 220
Thr Gly Asn Asp Phe Ser Thr Leu Tyr Ala Pro Leu Ile Arg Asp Gly
225                 230                 235                 240
Arg Met Glu Lys Phe Tyr Trp Ala Pro Thr Arg Glu Asp Arg Ile Gly
                245                 250                 255
Val Cys Lys Gly Ile Phe Arg Thr Asp Lys Ile Lys Asp Glu Asp Ile
            260                 265                 270
Val Thr Leu Val Asp Gln Phe Pro Gly Gln Ser Ile Asp Phe Phe Gly
        275                 280                 285
Ala Leu Arg Ala Arg Val Tyr Asp Asp Glu Val Arg Lys Phe Val Glu
    290                 295                 300
Ser Leu Gly Val Glu Lys Ile Gly Lys Arg Leu Val Asn Ser Arg Glu
305                 310                 315                 320
Gly Pro Pro Val Phe Glu Gln Pro Glu Met Thr Tyr Glu Lys Leu Met
                325                 330                 335
Glu Tyr Gly Asn Met Leu Val Met Glu Gln Glu Asn Val Lys Arg Val
            340                 345                 350
Gln Leu Ala Glu Thr Tyr Leu Ser Gln Ala Ala Leu Gly Asp Ala Asn
        355                 360                 365
Ala Asp Ala Ile Gly Arg Gly Thr Phe Tyr Gly Lys Thr Glu Glu Lys
    370                 375                 380
Glu Pro Ser Lys Leu Glu
385                 390

<210> SEQ ID NO 7
<211> LENGTH: 1173
<212> TYPE: DNA
<213> ORGANISM: Artificial Sequence
<220> FEATURE:
<223> OTHER INFORMATION: Based on Arabidopsis thaliana sequence

<400> SEQUENCE: 7
atggtgaaag aagacaaaca aaccgatgga gacagatgga gaggtcttgc ctacgacact      60
tctgatgatc aacaagacat caccagaggc aagggtatgg ttgactctgt cttccaagct     120
cctatgggaa ccggaactca ccacgctgtc cttagctcat acgaatacgt tagccaaggc     180
cttaggcagt acaacttgga caacatgatg gatgggtttt acattgctcc tgctttcatg     240
gacaagcttg ttgttcacat caccaagaac ttcttgactc tgcctaacat caaggttcca     300
cttattttgg gtatatgggg aggcaaaggt caaggtaaat ccttccagtg tgagcttgtc     360
atggccaaga tgggtatcaa cccaatcatg atgagtgctg agagcttgat gagtggaaac     420
gcaggagaac ccgcaaagct tatccgtcag aggtaccgtg aggcagctga tttgatcaag     480
aagggaagaa tgtgttgtct cttcatcaac gatcttgacg ctggtgcggg tcgtatgggt     540
ggtactactc agtacactgt caacaaccag atggttaacg caacactcat gaacattgct     600
gataacccaa ccaacgtcca gctcccagga atgtacaaca aggaagagaa cgcacgtgtc     660
cccatcattt gcactggtaa cgatttctcc accctatacg ctcctctcat ccgtgatgga     720
```

```
cgtatggaga agttctactg ggccccgacc cgtgaagacc gtatcggtgt ctgcaagggt    780
atcttcagaa ctgacaagat caaggacgaa gacattgtca gacttgttga tcagttccct    840
ggtcaatcta tcgatttctt cggtgctttg agggcgagag tgtacgatga tgaagtgagg    900
aagttcgttg agagccttgg agttgagaag atcggaaaga ggctggttaa ctcaagggaa    960
ggacctcccg tgttcgagca acccgagatg acttatgaga agcttatgga atacggaaac   1020
atgcttgtga tggaacaaga gaatgtcaag agagtccaac ttgccgagac ctacctcagc   1080
caggctgctc tgggagacgc aaacgctgac gccatcggcc gcggaacttt ctacggtaaa   1140
acagaggaaa aggagcccag caagctcgag taa                                1173
```

<210> SEQ ID NO 8
<211> LENGTH: 390
<212> TYPE: PRT
<213> ORGANISM: Artificial Sequence
<220> FEATURE:
<223> OTHER INFORMATION: Based on Arabidopsis thaliana sequence

<400> SEQUENCE: 8

```
Met Val Lys Glu Asp Lys Gln Thr Asp Gly Asp Arg Trp Arg Gly Leu
 1               5                  10                  15

Ala Tyr Asp Thr Ser Asp Asp Gln Gln Asp Ile Thr Arg Gly Lys Gly
            20                  25                  30

Met Val Asp Ser Val Phe Gln Ala Pro Met Gly Thr Gly Thr His His
        35                  40                  45

Ala Val Leu Ser Ser Tyr Glu Tyr Val Ser Gln Gly Leu Arg Gln Tyr
    50                  55                  60

Asn Leu Asp Asn Met Met Asp Gly Phe Tyr Ile Ala Pro Ala Phe Met
65                  70                  75                  80

Asp Lys Leu Val Val His Ile Thr Lys Asn Phe Leu Thr Leu Pro Asn
                85                  90                  95

Ile Lys Val Pro Leu Ile Leu Gly Ile Trp Gly Gly Lys Gly Gln Gly
            100                 105                 110

Lys Ser Phe Gln Cys Glu Leu Val Met Ala Lys Met Gly Ile Asn Pro
        115                 120                 125

Ile Met Met Ser Ala Gly Glu Leu Glu Ser Gly Asn Ala Gly Glu Pro
    130                 135                 140

Ala Lys Leu Ile Arg Gln Arg Tyr Arg Glu Ala Ala Asp Leu Ile Lys
145                 150                 155                 160

Lys Gly Lys Met Cys Cys Leu Phe Ile Asn Asp Leu Asp Ala Gly Ala
                165                 170                 175

Gly Arg Met Gly Gly Thr Thr Gln Tyr Thr Val Asn Asn Gln Met Val
            180                 185                 190

Asn Ala Thr Leu Met Asn Ile Ala Asp Asn Pro Thr Asn Val Gln Leu
        195                 200                 205

Pro Gly Met Tyr Asn Lys Glu Glu Asn Ala Arg Val Pro Ile Ile Cys
    210                 215                 220

Thr Gly Asn Asp Phe Ser Thr Leu Tyr Ala Pro Leu Ile Arg Asp Gly
225                 230                 235                 240

Arg Met Glu Lys Phe Tyr Trp Ala Pro Thr Arg Glu Asp Arg Ile Gly
                245                 250                 255

Val Cys Lys Gly Ile Phe Arg Thr Asp Lys Ile Lys Asp Glu Asp Ile
            260                 265                 270

Val Arg Leu Val Asp Gln Phe Pro Gly Gln Ser Ile Asp Phe Phe Gly
        275                 280                 285
```

Ala Leu Arg Ala Arg Val Tyr Asp Asp Glu Val Arg Lys Phe Val Glu
        290                 295                 300

Ser Leu Gly Val Glu Lys Ile Gly Lys Arg Leu Val Asn Ser Arg Glu
305                 310                 315                 320

Gly Pro Pro Val Phe Glu Gln Pro Glu Met Thr Tyr Glu Lys Leu Met
                325                 330                 335

Glu Tyr Gly Asn Met Leu Val Met Glu Gln Glu Asn Val Lys Arg Val
            340                 345                 350

Gln Leu Ala Glu Thr Tyr Leu Ser Gln Ala Ala Leu Gly Asp Ala Asn
        355                 360                 365

Ala Asp Ala Ile Gly Arg Gly Thr Phe Tyr Gly Lys Thr Glu Glu Lys
    370                 375                 380

Glu Pro Ser Lys Leu Glu
385                 390

<210> SEQ ID NO 9
<211> LENGTH: 1173
<212> TYPE: DNA
<213> ORGANISM: Artificial Sequence
<220> FEATURE:
<223> OTHER INFORMATION: Based on Arabidopsis thaliana sequence

<400> SEQUENCE: 9
atggtgaaag aagacaaaca aaccgatgga gacagatgga gaggtcttgc ctacgacact      60
tctgatgatc aacaagacat caccagaggc aagggtatgg ttgactctgt cttccaagct     120
cctatgggaa ccggaactca ccacgctgtc cttagctcat acgaatacgt tagccaaggc     180
cttaggcagt acaacttgga caacatgatg gatgggtttt acattgctcc tgctttcatg     240
gacaagcttg ttgttcacat caccaagaac ttcttgactc tgcctaacat caaggttcca     300 cttatttttgg gtatatgggg aggcaaaggt caaggtaaat ccttccagtg tgagcttgtc     360
atggccaaga tgggtatcaa cccaatcatg atgagtgctg gagagcttga gagtggaaac     420
gcaggagaac ccgcaaagct tatccgtcag aggtaccgtg aggcagctga cttgatcaag     480
aagggaaaga tgtgttgtct cttcatcaac gatcttgacg ctggtgcggg tcgtatggga     540
ggtactactc agtacactgt caacaaccag atggttaacg caacactcat gaacattgct     600
gataacccaa ccaacgtcca gctcccagga atgtacaaca aggaagagaa cgcacgtgtc     660
cccatcattt gcactggtaa cgatttctcc accctatacg ctcctctcat ccgtgatgga     720
cgtatggaga agttctactg gccccgacc cgtgaagacc gtatcggtgt ctgcaagggt     780
atcttcagaa ctgacaagat caaggacgaa gacattgtca cacttgttga tcagttccct     840
ggtcaatcta tcgatttctt cggtgctttg agggcgagag tgtacgatga tgaagtgagg     900
aagttcgttg agagccttgg agttgagaat atcggaaaga ggctggttaa ctcaagggaa     960 ggacctccg tgttcgagca acccgagatg acttatgaga gcttatggaa atacggaaac    1020
atgcttgtga tggaacaaga gaatgtcaag agagtccaac ttgccgagac ctacctcagc    1080
caggctgctt gggagacgc aaacgctgac gccatcggcc gcggaacttt ctacggtaaa    1140
acagaggaaa aggagcccag caagctcgag taa                                  1173

<210> SEQ ID NO 10
<211> LENGTH: 390
<212> TYPE: PRT
<213> ORGANISM: Artificial Sequence
<220> FEATURE:
<223> OTHER INFORMATION: Based on Arabidopsis thaliana sequence

<400> SEQUENCE: 10

```
Met Val Lys Glu Asp Lys Gln Thr Asp Gly Asp Arg Trp Arg Gly Leu
 1               5                  10                  15

Ala Tyr Asp Thr Ser Asp Gln Gln Asp Ile Thr Arg Gly Lys Gly
             20                  25                  30

Met Val Asp Ser Val Phe Gln Ala Pro Met Gly Thr Gly Thr His His
             35                  40                  45

Ala Val Leu Ser Ser Tyr Glu Tyr Val Ser Gln Gly Leu Arg Gln Tyr
 50                  55                  60

Asn Leu Asp Asn Met Met Asp Gly Phe Tyr Ile Ala Pro Ala Phe Met
 65                  70                  75                  80

Asp Lys Leu Val Val His Ile Thr Lys Asn Phe Leu Thr Leu Pro Asn
                 85                  90                  95

Ile Lys Val Pro Leu Ile Leu Gly Ile Trp Gly Gly Lys Gly Gln Gly
                 100                 105                 110

Lys Ser Phe Gln Cys Glu Leu Val Met Ala Lys Met Gly Ile Asn Pro
             115                 120                 125

Ile Met Met Ser Ala Gly Glu Leu Glu Ser Gly Asn Ala Gly Glu Pro
 130                 135                 140

Ala Lys Leu Ile Arg Gln Arg Tyr Arg Glu Ala Ala Asp Leu Ile Lys
 145                 150                 155                 160

Lys Gly Lys Met Cys Cys Leu Phe Ile Asn Asp Leu Asp Ala Gly Ala
                 165                 170                 175

Gly Arg Met Gly Gly Thr Thr Gln Tyr Thr Val Asn Asn Gln Met Val
             180                 185                 190

Asn Ala Thr Leu Met Asn Ile Ala Asp Asn Pro Thr Asn Val Gln Leu
             195                 200                 205

Pro Gly Met Tyr Asn Lys Glu Glu Asn Ala Arg Val Pro Ile Ile Cys
 210                 215                 220

Thr Gly Asn Asp Phe Ser Thr Leu Tyr Ala Pro Leu Ile Arg Asp Gly
225                 230                 235                 240

Arg Met Glu Lys Phe Tyr Trp Ala Pro Thr Arg Glu Asp Arg Ile Gly
                 245                 250                 255

Val Cys Lys Gly Ile Phe Arg Thr Asp Lys Ile Lys Asp Glu Asp Ile
                 260                 265                 270

Val Thr Leu Val Asp Gln Phe Pro Gly Gln Ser Ile Asp Phe Phe Gly
             275                 280                 285

Ala Leu Arg Ala Arg Val Tyr Asp Asp Glu Val Arg Lys Phe Val Glu
             290                 295                 300

Ser Leu Gly Val Glu Asn Ile Gly Lys Arg Leu Val Asn Ser Arg Glu
305                 310                 315                 320

Gly Pro Pro Val Phe Glu Gln Pro Glu Met Thr Tyr Glu Lys Leu Met
                 325                 330                 335

Glu Tyr Gly Asn Met Leu Val Met Glu Gln Glu Asn Val Lys Arg Val
             340                 345                 350

Gln Leu Ala Glu Thr Tyr Leu Ser Gln Ala Ala Leu Gly Asp Ala Asn
             355                 360                 365

Ala Asp Ala Ile Gly Arg Gly Thr Phe Tyr Gly Lys Thr Glu Glu Lys
 370                 375                 380

Glu Pro Ser Lys Leu Glu
 385                 390

<210> SEQ ID NO 11
<211> LENGTH: 1173
<212> TYPE: DNA
```

<213> ORGANISM: Artificial Sequence
<220> FEATURE:
<223> OTHER INFORMATION: Based on Arabidopsis thaliana sequence

<400> SEQUENCE: 11

```
atggtgaaag aagacaaaca aaccgatgga gacagatgga gaggtcttgc ctacgacact    60
tctgatgatc aacaagacat caccagaggc aagggtatgg ttgactctgt cttccaagct   120
cctacgggaa ccggaactca ccacgctgtc cttagctcat acgaatacgt tagccaaggc   180
cttaggcagt acaacttgga caacatgatg gatgggtttt acattgctcc tgctttcatg   240
gacaagcttg ttgttcacat caccaagaac ttcttgactc tgcctaacat caaggttcca   300
cttatttttgg gtatatgggg aggcaaaggt caaggtaaat ccttccagtg tgagcttgtc   360
atggccaaga tgggtatcaa cccaatcatg ataagtgctg agagcttga gagtggaaac   420
gcaggagaac ccgcaaagct tatccgtcag aggtaccgtg aggcagctga cttgatcaag   480
aagggaaaga tgtgttgtct cttcatcaac gatcttgacg ctggtgcggg tcgtatgggt   540
ggtactactc agtacactgt caacaaccag atggttaacg caacactcat gaacattgct   600
gataacccaa ccaacgtcca gctcccagga atgtacaaca aggaagagaa cgcacgtgtc   660
cccatcattt gcactggtaa cgatttctcc accctatacg ctcctctcat ccgtgatgga   720
cgtatggaga agttctactg gccccgacc cgtgaagacc gtatcggtgt ctgcaagggt   780
atcttcagaa ctgacaagat caaggacgaa gacattgtca cacttgttga tcagttccct   840
ggtcaatcta tcgatttctt cggtgctttg agggcgaaag tgtacgatga tgaagtgagg   900
aagttcgttg agagccttgg agttgagaag atcggaaaga ggctggttaa ctcaagggaa   960
ggacctcccg tgttcgagca acccgagatg acttatgaga agcttatgga atacggaaac  1020
atgctcgtga tggaacaaga gaatgtcaag agagtccaac ttgccgagac ctacctcagc  1080
caggctgctt tgggagacgc aaacgctgac gccatcggcc gcggaacttt ctacggtaaa  1140
acagaggaaa aggagcccag caagctcgag taa                                1173
```

<210> SEQ ID NO 12
<211> LENGTH: 390
<212> TYPE: PRT
<213> ORGANISM: Artificial Sequence
<220> FEATURE:
<223> OTHER INFORMATION: Based on Arabidopsis thaliana sequence

<400> SEQUENCE: 12

```
Met Val Lys Glu Asp Lys Gln Thr Asp Gly Asp Arg Trp Arg Gly Leu
  1               5                  10                  15

Ala Tyr Asp Thr Ser Asp Asp Gln Gln Asp Ile Thr Arg Gly Lys Gly
             20                  25                  30

Met Val Asp Ser Val Phe Gln Ala Pro Thr Gly Thr Gly Thr His His
         35                  40                  45

Ala Val Leu Ser Ser Tyr Glu Tyr Val Ser Gln Gly Leu Arg Gln Tyr
     50                  55                  60

Asn Leu Asp Asn Met Met Asp Gly Phe Tyr Ile Ala Pro Ala Phe Met
 65                  70                  75                  80

Asp Lys Leu Val Val His Ile Thr Lys Asn Phe Leu Thr Leu Pro Asn
                 85                  90                  95

Ile Lys Val Pro Leu Ile Leu Gly Ile Trp Gly Gly Lys Gly Gln Gly
            100                 105                 110

Lys Ser Phe Gln Cys Glu Leu Val Met Ala Lys Met Gly Ile Asn Pro
        115                 120                 125
```

```
Ile Met Ile Ser Ala Gly Glu Leu Glu Ser Gly Asn Ala Gly Glu Pro
            130                 135                 140

Ala Lys Leu Ile Arg Gln Arg Tyr Arg Glu Ala Ala Asp Leu Ile Lys
145                 150                 155                 160

Lys Gly Lys Met Cys Cys Leu Phe Ile Asn Asp Leu Asp Ala Gly Ala
                165                 170                 175

Gly Arg Met Gly Gly Thr Thr Gln Tyr Thr Val Asn Asn Gln Met Val
            180                 185                 190

Asn Ala Thr Leu Met Asn Ile Ala Asp Asn Pro Thr Asn Val Gln Leu
            195                 200                 205

Pro Gly Met Tyr Asn Lys Glu Asn Ala Arg Val Pro Ile Ile Cys
210                 215                 220

Thr Gly Asn Asp Phe Ser Thr Leu Tyr Ala Pro Leu Ile Arg Asp Gly
225                 230                 235                 240

Arg Met Glu Lys Phe Tyr Trp Ala Pro Thr Arg Glu Asp Arg Ile Gly
                245                 250                 255

Val Cys Lys Gly Ile Phe Arg Thr Asp Lys Ile Lys Asp Glu Asp Ile
                260                 265                 270

Val Thr Leu Val Asp Gln Phe Pro Gly Gln Ser Ile Asp Phe Phe Gly
            275                 280                 285

Ala Leu Arg Ala Lys Val Tyr Asp Asp Glu Val Arg Lys Phe Val Glu
290                 295                 300

Ser Leu Gly Val Glu Lys Ile Gly Lys Arg Leu Val Asn Ser Arg Glu
305                 310                 315                 320

Gly Pro Pro Val Phe Glu Gln Pro Glu Met Thr Tyr Glu Lys Leu Met
                325                 330                 335

Glu Tyr Gly Asn Met Leu Val Met Glu Gln Glu Asn Val Lys Arg Val
            340                 345                 350

Gln Leu Ala Glu Thr Tyr Leu Ser Gln Ala Ala Leu Gly Asp Ala Asn
            355                 360                 365

Ala Asp Ala Ile Gly Arg Gly Thr Phe Tyr Gly Lys Thr Glu Glu Lys
370                 375                 380

Glu Pro Ser Lys Leu Glu
385                 390

<210> SEQ ID NO 13
<211> LENGTH: 1173
<212> TYPE: DNA
<213> ORGANISM: Artificial Sequence
<220> FEATURE:
<223> OTHER INFORMATION: Based on Arabidopsis thaliana sequence

<400> SEQUENCE: 13
atggtgaaag aagacaaaca aaccgatgga gacagatgga gaggtcttgc ctacgacact    60
tctgatgatc aacaagacat caccagaggc aagggtatgg ttgactctgt cttccaagct   120
cctacgggaa ccggaactca ccacgctgtc cttagctcat acgaatacgt tagccaaggc   180
cttaggcagt acaacttgga caacatgatg gatgggtttt acattgctcc tgctttcatg   240
gacaagcttg ttgttcacat caccaagaac ttcttgactc tgcctaacat caaggttcca   300
cttattttgg gtatatgggg aggcaaaggt caaggtaaat ccttccagtg tgagcttgtc   360
atggccaaga tgggtatcaa cccaatcatg atgagtgctg agagcttga gagtggaaac    420 gcaggagaac ccgcaaagct tatccgtcag aggtaccgtg aggcagctga tttgatcaag   480
aagggaagaa tgtgttgtct cttcatcaac gatcttgacg ctggtgcggg tcgtatgggt   540
ggtactactc agtacactgt caacaaccag atggttaacg caacactcat gaacattgct   600
```

```
gataacccaa ccaacgtcca gctcccagga atgtacaaca aggaagagaa cgcacgtgtc    660
cccatcattt gcactggtaa cgatttctcc accctatacg ctcctctcat ccgtgatgga    720
cgtatggaga agttctactg gccccgacc cgtgaagacc gtatcggtgt ctgcaagggt    780
atcttcagaa ctgacaagat caaggacgaa gacattgtca gacttgttga tcagttccct    840
ggtcaatcta tcgatttctt cggtgctttg agggcgagag tgtacgatga tgaagtgagg    900
aagttcgttg agagccttgg agttgagaag atcggaaaga ggctggttaa ctcaagggaa    960
ggacctcccg tgttcgagca acccgagatg acttatgaga agcttatgga atacggaaac   1020
atgctcgtga tggaacaaga gaatgtcaag agagtccaac ttgccgagac ctacctcagc   1080
caggctgctt tgggagacgc aaacgctgac gccatcggcc gcggaacttt ctacggtaaa   1140
acagaggaaa aggagcccag caagctcgag taa                                1173
```

<210> SEQ ID NO 14
<211> LENGTH: 390
<212> TYPE: PRT
<213> ORGANISM: Artificial Sequence
<220> FEATURE:
<223> OTHER INFORMATION: Based on Arabidopsis thaliana sequence

<400> SEQUENCE: 14

```
Met Val Lys Glu Asp Lys Gln Thr Asp Gly Asp Arg Trp Arg Gly Leu
  1               5                  10                  15

Ala Tyr Asp Thr Ser Asp Asp Gln Gln Asp Ile Thr Arg Gly Lys Gly
             20                  25                  30

Met Val Asp Ser Val Phe Gln Ala Pro Thr Gly Thr Gly Thr His His
         35                  40                  45

Ala Val Leu Ser Ser Tyr Glu Tyr Val Ser Gln Gly Leu Arg Gln Tyr
     50                  55                  60

Asn Leu Asp Asn Met Met Asp Gly Phe Tyr Ile Ala Pro Ala Phe Met
 65                  70                  75                  80

Asp Lys Leu Val Val His Ile Thr Lys Asn Phe Leu Thr Leu Pro Asn
                 85                  90                  95

Ile Lys Val Pro Leu Ile Leu Gly Ile Trp Gly Lys Gly Gln Gly
            100                 105                 110

Lys Ser Phe Gln Cys Glu Leu Val Met Ala Lys Met Gly Ile Asn Pro
        115                 120                 125

Ile Met Met Ser Ala Gly Glu Leu Glu Ser Gly Asn Ala Gly Glu Pro
    130                 135                 140

Ala Lys Leu Ile Arg Gln Arg Tyr Arg Glu Ala Ala Asp Leu Ile Lys
145                 150                 155                 160

Lys Gly Lys Met Cys Cys Leu Phe Ile Asn Asp Leu Asp Ala Gly Ala
                165                 170                 175

Gly Arg Met Gly Gly Thr Thr Gln Tyr Thr Val Asn Asn Gln Met Val
            180                 185                 190

Asn Ala Thr Leu Met Asn Ile Ala Asp Asn Pro Thr Asn Val Gln Leu
        195                 200                 205

Pro Gly Met Tyr Asn Lys Glu Glu Asn Ala Arg Val Pro Ile Ile Cys
    210                 215                 220

Thr Gly Asn Asp Phe Ser Thr Leu Tyr Ala Pro Leu Ile Arg Asp Gly
225                 230                 235                 240

Arg Met Glu Lys Phe Tyr Trp Ala Pro Thr Arg Glu Asp Arg Ile Gly
                245                 250                 255

Val Cys Lys Gly Ile Phe Arg Thr Asp Lys Ile Lys Asp Glu Asp Ile
```

```
                260             265             270
Val Arg Leu Val Asp Gln Phe Pro Gly Gln Ser Ile Asp Phe Phe Gly
            275                 280                 285

Ala Leu Arg Ala Arg Val Tyr Asp Asp Glu Val Arg Lys Phe Val Glu
        290                 295                 300

Ser Leu Gly Val Glu Lys Ile Gly Lys Arg Leu Val Asn Ser Arg Glu
305                 310                 315                 320

Gly Pro Pro Val Phe Glu Gln Pro Glu Met Thr Tyr Glu Lys Leu Met
                325                 330                 335

Glu Tyr Gly Asn Met Leu Val Met Glu Gln Glu Asn Val Lys Arg Val
            340                 345                 350

Gln Leu Ala Glu Thr Tyr Leu Ser Gln Ala Ala Leu Gly Asp Ala Asn
        355                 360                 365

Ala Asp Ala Ile Gly Arg Gly Thr Phe Tyr Gly Lys Thr Glu Glu Lys
    370                 375                 380

Glu Pro Ser Lys Leu Glu
385                 390

<210> SEQ ID NO 15
<211> LENGTH: 1173
<212> TYPE: DNA
<213> ORGANISM: Artificial Sequence
<220> FEATURE:
<223> OTHER INFORMATION: Based on Arabidopsis thaliana sequence

<400> SEQUENCE: 15
atggtgaaag aagacaaaca aaccgatgga gacagatgga gaggtcttgc ctacgacact      60
tctgatgatc aacaagacat caccagaggc aagggtatgg ttgactctgt cttccaagct     120
cctatgggaa ccggaactca ccacgctgtc cttagctcat acgaatacgt tagccaaggc     180
cttaggcagt acaacttgga caacatgatg gatgggtttt acattgctcc tgctttcatg     240
gacaagcttg ttgttcacat caccaagaac ttcttgactc tgcctaacat caaggttcca     300
cttattttgg gtatatgggg aggcaaaggt caaggtaaat ccttccagtg tgagcttgtc     360
atggccaaga tgggtatcaa cccaatcatg gtgagtgctg agagcttga gagtggaaac      420 gcaggagaac ccgcaaagct tatccgtcag aggtaccgtg aggcagctga tttgatcaag     480
aagggaaaga tgtgttgtct cttcatcaac gatcttgacg ctggtgcggg tcgtatgggt     540
ggtactactc agtacactgt caacaaccag atggttaacg caacactcat gaacattgct     600
gataacccaa ccaacgtcca gctcccagga atgtacaaca ggaagagaaa cgcacgtgtc     660
cccatcattt gcactggtaa cgatttctcc accctatacg ctcctctcat ccgtgatgga     720
cgtatggaga agttctactg gcccccgacc cgtgaagacc gtatcggtat atgcaagggt     780
atcttcagaa ctgacaagat caaggacgaa gacattgtca cacttgttga tcagttccct     840
ggtcaatcta tcgatttctt cggtgctttg agggcgagag tgtacgatga tgaagtgagg     900
aagttcgttg agagccttgg agttgagaat atcggaaaga ggctggttaa ctcaagggaa     960
ggacctcccg tgttcgagca acccgagatg acttatgaga agcttatgga atacggaaac    1020
atgcttgtga tggaacaaga gaatgtcaag agagtccaac ttgccgagac ctacctcagc    1080
caggctgctt gggagacgc aaacgctgac gccatcggcc gcggaacttt ctacggtaaa     1140
acagaggaaa aggagcccag caagctcgag taa                                 1173

<210> SEQ ID NO 16
<211> LENGTH: 390
<212> TYPE: PRT
```

<213> ORGANISM: Artificial Sequence
<220> FEATURE:
<223> OTHER INFORMATION: Based on Arabidopsis thaliana sequence

<400> SEQUENCE: 16

```
Met Val Lys Glu Asp Lys Gln Thr Asp Gly Asp Arg Trp Arg Gly Leu
 1               5                  10                  15

Ala Tyr Asp Thr Ser Asp Asp Gln Gln Asp Ile Thr Arg Gly Lys Gly
                20                  25                  30

Met Val Asp Ser Val Phe Gln Ala Pro Met Gly Thr Gly Thr His His
                35                  40                  45

Ala Val Leu Ser Ser Tyr Glu Tyr Val Ser Gln Gly Leu Arg Gln Tyr
 50                  55                  60

Asn Leu Asp Asn Met Met Asp Gly Phe Tyr Ile Ala Pro Ala Phe Met
65                   70                  75                  80

Asp Lys Leu Val Val His Ile Thr Lys Asn Phe Leu Thr Leu Pro Asn
                85                  90                  95

Ile Lys Val Pro Leu Ile Leu Gly Ile Trp Gly Lys Gly Gln Gly
                100                 105                 110

Lys Ser Phe Gln Cys Glu Leu Val Met Ala Lys Met Gly Ile Asn Pro
            115                 120                 125

Ile Met Val Ser Ala Gly Glu Leu Glu Ser Gly Asn Ala Gly Glu Pro
130                 135                 140

Ala Lys Leu Ile Arg Gln Arg Tyr Arg Glu Ala Ala Asp Leu Ile Lys
145                 150                 155                 160

Lys Gly Lys Met Cys Cys Leu Phe Ile Asn Asp Leu Asp Ala Gly Ala
                165                 170                 175

Gly Arg Met Gly Gly Thr Thr Gln Tyr Thr Val Asn Asn Gln Met Val
            180                 185                 190

Asn Ala Thr Leu Met Asn Ile Ala Asp Asn Pro Thr Asn Val Gln Leu
            195                 200                 205

Pro Gly Met Tyr Asn Lys Glu Glu Asn Ala Arg Val Pro Ile Ile Cys
            210                 215                 220

Thr Gly Asn Asp Phe Ser Thr Leu Tyr Ala Pro Leu Ile Arg Asp Gly
225                 230                 235                 240

Arg Met Glu Lys Phe Tyr Trp Ala Pro Thr Arg Glu Asp Arg Ile Gly
                245                 250                 255

Ile Cys Lys Gly Ile Phe Arg Thr Asp Lys Ile Lys Asp Glu Asp Ile
            260                 265                 270

Val Thr Leu Val Asp Gln Phe Pro Gly Gln Ser Ile Asp Phe Phe Gly
            275                 280                 285

Ala Leu Arg Ala Arg Val Tyr Asp Asp Glu Val Arg Lys Phe Val Glu
290                 295                 300

Ser Leu Gly Val Glu Asn Ile Gly Lys Arg Leu Val Asn Ser Arg Glu
305                 310                 315                 320

Gly Pro Pro Val Phe Glu Gln Pro Glu Met Thr Tyr Glu Lys Leu Met
                325                 330                 335

Glu Tyr Gly Asn Met Leu Val Met Glu Gln Asn Val Lys Arg Val
                340                 345                 350

Gln Leu Ala Glu Thr Tyr Leu Ser Gln Ala Ala Leu Gly Asp Ala Asn
            355                 360                 365

Ala Asp Ala Ile Gly Arg Gly Thr Phe Tyr Gly Lys Thr Glu Glu Lys
370                 375                 380

Glu Pro Ser Lys Leu Glu
385                 390
```

<210> SEQ ID NO 17
<211> LENGTH: 1173
<212> TYPE: DNA
<213> ORGANISM: Artificial Sequence
<220> FEATURE:
<223> OTHER INFORMATION: Based on Arabidopsis thaliana sequence

<400> SEQUENCE: 17

| | |
|---|---|
| atggtgaaag aagacaaaca aaccgatgga gacagatgga gaggtcttgc ctacgacact | 60 |
| tctgatgatc aacaagacat caccagaggc aagggtatgg ttgactctgt cttccaagct | 120 |
| cctatgggaa ccggaactca ccacgctgtc cttagctcat acgaatacgt tagccaaggc | 180 |
| cttaggcagt acaacttgga caacatgatg gatgggtttt acattgctcc tgctttcatg | 240 |
| gacaagcttg ttgttcacat caccaagaac ttcttgactc tgcctaacat caaggttcca | 300 |
| cttattttgg gtatatgggg aggcaaaggt caaggtaaat ccttccagtg tgagcttgtc | 360 |
| atggccaaga tgggtatcaa cccaatcatg atgagtgctg gagagcttga gagtggaaac | 420 |
| gcaggagaac ccgcaaagct tatccgtcag aggtaccgtg aggcagctga cttgatcaag | 480 |
| aagggaaaga tgtgttgtct cctcatcaac gatcttgacg ctggtgcggg tcgtatgggt | 540 |
| ggtactactc agtacactgt caacaaccag atggttaacg caacactcat gaacattgct | 600 |
| gataacccaa ccaacgtcca gctcccagga atgtacaaca aggaagagaa cgcacgtgtc | 660 |
| cccatcattt gcactggtaa cgatttctcc accctatacg ctcctctcat ccgtgatgga | 720 |
| cgtatggaga agttctactg gccccgacc cgtgaagacc gtatcggtat atgcaagggt | 780 |
| atcttcagaa ctgacaagat caaggacgaa gacattgtca gacttgttga tcagttccct | 840 |
| ggtcaatcta tcgatttctt cggtgctttg agggcgagag tgtacgatga tgaagtgagg | 900 |
| aagttcgttg agagccttgg agttgagaat atcggaaaga ggctggttaa ctcaagggaa | 960 |
| ggacctcccg tgttcgagca acccgagatg acttatgaga agcttatgga atacggaaac | 1020 |
| atgcttgtga tggaacaaga gaatgtcaag agagtccaac ttgccgagac ctacctcagc | 1080 |
| caggctgctc tgggagacgc aaacgctgac gccatcggcc gcggaacttt ctacggtaaa | 1140 |
| acagaggaaa aggagcccag caagctcgag taa | 1173 |

<210> SEQ ID NO 18
<211> LENGTH: 390
<212> TYPE: PRT
<213> ORGANISM: Artificial Sequence
<220> FEATURE:
<223> OTHER INFORMATION: Based on Arabidopsis thaliana sequence

<400> SEQUENCE: 18

Met Val Lys Glu Asp Lys Gln Thr Asp Gly Asp Arg Trp Arg Gly Leu
 1               5                  10                  15

Ala Tyr Asp Thr Ser Asp Asp Gln Gln Asp Ile Thr Arg Gly Lys Gly
            20                  25                  30

Met Val Asp Ser Val Phe Gln Ala Pro Met Gly Thr Gly Thr His His
        35                  40                  45

Ala Val Leu Ser Ser Tyr Glu Tyr Val Ser Gln Gly Leu Arg Gln Tyr
    50                  55                  60

Asn Leu Asp Asn Met Met Asp Gly Phe Tyr Ile Ala Pro Ala Phe Met
65                  70                  75                  80

Asp Lys Leu Val Val His Ile Thr Lys Asn Phe Leu Thr Leu Pro Asn
                85                  90                  95

Ile Lys Val Pro Leu Ile Leu Gly Ile Trp Gly Gly Lys Gly Gln Gly

```
                          100                 105                 110
Lys Ser Phe Gln Cys Glu Leu Val Met Ala Lys Met Gly Ile Asn Pro
            115                 120                 125
Ile Met Met Ser Ala Gly Glu Leu Glu Ser Gly Asn Ala Gly Glu Pro
        130                 135                 140
Ala Lys Leu Ile Arg Gln Arg Tyr Arg Glu Ala Ala Asp Leu Ile Lys
145                 150                 155                 160
Lys Gly Lys Met Cys Cys Leu Leu Ile Asn Asp Leu Asp Ala Gly Ala
                165                 170                 175
Gly Arg Met Gly Gly Thr Thr Gln Tyr Thr Val Asn Asn Gln Met Val
            180                 185                 190
Asn Ala Thr Leu Met Asn Ile Ala Asp Asn Pro Thr Asn Val Gln Leu
        195                 200                 205
Pro Gly Met Tyr Asn Lys Glu Glu Asn Ala Arg Val Pro Ile Ile Cys
    210                 215                 220
Thr Gly Asn Asp Phe Ser Thr Leu Tyr Ala Pro Leu Ile Arg Asp Gly
225                 230                 235                 240
Arg Met Glu Lys Phe Tyr Trp Ala Pro Thr Arg Glu Asp Arg Ile Gly
                245                 250                 255
Ile Cys Lys Gly Ile Phe Arg Thr Asp Lys Ile Lys Asp Glu Asp Ile
            260                 265                 270
Val Arg Leu Val Asp Gln Phe Pro Gly Gln Ser Ile Asp Phe Phe Gly
        275                 280                 285
Ala Leu Arg Ala Arg Val Tyr Asp Asp Glu Val Arg Lys Phe Val Glu
    290                 295                 300
Ser Leu Gly Val Glu Asn Ile Gly Lys Arg Leu Val Asn Ser Arg Glu
305                 310                 315                 320
Gly Pro Pro Val Phe Glu Gln Pro Glu Met Thr Tyr Glu Lys Leu Met
                325                 330                 335
Glu Tyr Gly Asn Met Leu Val Met Glu Gln Asn Val Lys Arg Val
            340                 345                 350
Gln Leu Ala Glu Thr Tyr Leu Ser Gln Ala Ala Leu Gly Asp Ala Asn
        355                 360                 365
Ala Asp Ala Ile Gly Arg Gly Thr Phe Tyr Gly Lys Thr Glu Glu Lys
    370                 375                 380
Glu Pro Ser Lys Leu Glu
385                 390

<210> SEQ ID NO 19
<211> LENGTH: 1173
<212> TYPE: DNA
<213> ORGANISM: Artificial Sequence
<220> FEATURE:
<223> OTHER INFORMATION: Based on Arabidopsis thaliana sequence

<400> SEQUENCE: 19
atggtgaaag aagacaaaca aaccgacgga gacagatgga gaggtcttgc ctacgacact    60
tctgatgatc aacaagacat caccagaggc aagggtatgg ttgactctgt cttccaagct   120
cctatgggaa ccggaactca ccacgctgtc cttagctcat acgaatacgt tagccaaggc   180
cttaggcagt acaacttgga caacatgatg gatgggtttt acattgctcc tgctttcatg   240
gacaagcttg ttgttcacat caccaagaac ttcttgactc tgcctaacat caaggttcca   300
cttattttgg gtatatgggg aggcaaaggt caaggtaaat ccttccagtg tgagcttgtc   360
atggccaaga tgggtatcaa cccaatcatg atgagtgctg gagagcttga gagtggaaac   420
```

-continued

```
gcaggagaac ccgcaaagct tatccgtcag aggtaccgtg aggcagctga cttgatcaag      480 aaggaaaga tgtgttgtct cctcatcaac gatcttgacg ctggtgcggg tcgtatgggt       540
ggtactactc agtacactgt caacaaccag atggttaacg caacactcat gaacattgct     600
gataacccaa ccaacgtcca gctcccagga atgtacaaca aggaagagaa cgcacgtgtc     660
cccatcattt gcactggtaa cgatttctcc accctatacg ctcctctcat ccgtgatgga      720
cgtatggaga agttctactg gccccgaccc gtgaagacc gtatcggtat atgcaagggt       780
atcttcagaa ctgacaagat caaggacgaa gacattgtca cacttgttga tcagttccct     840
ggtcaatcta tcgatttctt cggtgctttg agggcgagag tgtacgatga tgaagtgagg     900
aagttcgttg agagccttgg agttgagaat atcggaaaga ggctggttaa ctcaagggaa     960
ggacctcccg tgttcgagca acccgagatg acttatgaga agcttatgga atacggaaac    1020
atgctcgtga tggaacaaga gaatgtcaag agagtccaac ttgccgagac ctacctcagc    1080
caggctgctt tggagacgc aaacgctgac gccatcggcc gcggaacttt ctacggtaaa     1140
acagaggaaa aggagcccag caagctcgag taa                                   1173
```

<210> SEQ ID NO 20
<211> LENGTH: 390
<212> TYPE: PRT
<213> ORGANISM: Artificial Sequence
<220> FEATURE:
<223> OTHER INFORMATION: Based on Arabidopsis thaliana sequence

<400> SEQUENCE: 20

```
Met Val Lys Glu Asp Lys Gln Thr Asp Gly Asp Arg Trp Arg Gly Leu
 1               5                  10                  15

Ala Tyr Asp Thr Ser Asp Asp Gln Gln Asp Ile Thr Arg Gly Lys Gly
            20                  25                  30

Met Val Asp Ser Val Phe Gln Ala Pro Met Gly Thr Gly Thr His His
        35                  40                  45

Ala Val Leu Ser Ser Tyr Glu Tyr Val Ser Gln Gly Leu Arg Gln Tyr
    50                  55                  60

Asn Leu Asp Asn Met Met Asp Gly Phe Tyr Ile Ala Pro Ala Phe Met
65                  70                  75                  80

Asp Lys Leu Val Val His Ile Thr Lys Asn Phe Leu Thr Leu Pro Asn
                85                  90                  95

Ile Lys Val Pro Leu Ile Leu Gly Ile Trp Gly Gly Lys Gly Gln Gly
            100                 105                 110

Lys Ser Phe Gln Cys Glu Leu Val Met Ala Lys Met Gly Ile Asn Pro
        115                 120                 125

Ile Met Met Ser Ala Gly Glu Leu Glu Ser Gly Asn Ala Gly Glu Pro
    130                 135                 140

Ala Lys Leu Ile Arg Gln Arg Tyr Arg Glu Ala Ala Asp Leu Ile Lys
145                 150                 155                 160

Lys Gly Lys Met Cys Cys Leu Leu Ile Asn Asp Leu Asp Ala Gly Ala
                165                 170                 175

Gly Arg Met Gly Gly Thr Thr Gln Tyr Thr Val Asn Asn Gln Met Val
            180                 185                 190

Asn Ala Thr Leu Met Asn Ile Ala Asp Asn Pro Thr Asn Val Gln Leu
        195                 200                 205

Pro Gly Met Tyr Asn Lys Glu Glu Asn Ala Arg Val Pro Ile Ile Cys
    210                 215                 220

Thr Gly Asn Asp Phe Ser Thr Leu Tyr Ala Pro Leu Ile Arg Asp Gly
225                 230                 235                 240
```

```
Arg Met Glu Lys Phe Tyr Trp Ala Pro Thr Arg Glu Asp Arg Ile Gly
                245                 250                 255

Ile Cys Lys Gly Ile Phe Arg Thr Asp Lys Ile Lys Asp Glu Asp Ile
            260                 265                 270

Val Thr Leu Val Asp Gln Phe Pro Gly Gln Ser Ile Asp Phe Phe Gly
        275                 280                 285

Ala Leu Arg Ala Arg Val Tyr Asp Asp Glu Val Arg Lys Phe Val Glu
    290                 295                 300

Ser Leu Gly Val Glu Asn Ile Gly Lys Arg Leu Val Asn Ser Arg Glu
305                 310                 315                 320

Gly Pro Pro Val Phe Glu Gln Pro Glu Met Thr Tyr Glu Lys Leu Met
                325                 330                 335

Glu Tyr Gly Asn Met Leu Val Met Glu Gln Asn Val Lys Arg Val
            340                 345                 350

Gln Leu Ala Glu Thr Tyr Leu Ser Gln Ala Ala Leu Gly Asp Ala Asn
        355                 360                 365

Ala Asp Ala Ile Gly Arg Gly Thr Phe Tyr Gly Lys Thr Glu Glu Lys
    370                 375                 380

Glu Pro Ser Lys Leu Glu
385                 390

<210> SEQ ID NO 21
<211> LENGTH: 1173
<212> TYPE: DNA
<213> ORGANISM: Artificial Sequence
<220> FEATURE:
<223> OTHER INFORMATION: Based on Arabidopsis thaliana sequence

<400> SEQUENCE: 21
atggtgaaag aagacaaaca aaccgacgga gacagatgga gaggtcttgc ctacgacact      60
tctgatgatc aacaagacat caccagaggc aagggtatgg ttgactctgt cttccaagct     120
cctatgggaa ccggaactca ccacgctgtc cttagctcat acgaatacgt tagccaaggc     180
cttaggcagt acaacttgga caacatgatg gatgggtttt acattgctcc tgctttcatg     240
gacaagcttg ttgttcacat caccaagaac ttcttgactc tgcctaacat caaggttcca     300
cttattttgg gtatatgggg aggcaaaggt caaggtaaat ccttccagtg tgagcttgtc     360
atggccaaga tgggtatcaa cccaatcatg atgagtgctg agagcttga gagtggaaac     420 gcaggagaac ccgcaaagct tatccgtcag aggtaccgtg aggcagctga cttgatcaag     480
aagggaaaga tgtgttgtct cttcatcaac gatcttgacg ctggtgcggg tcgtatgggt     540
ggtactactc agtacactgt caacaaccag atggttaacg caacactcat gaacattgct     600
gataacccaa ccaacgtcca gctcccagga atgtacaaca ggaagagaa cgcacgtgtc     660 cccatcattt gcactggtaa cgatttctcc accctatacg ctcctctcat ccgtgatgga     720
cgtatggaga agttctactg gccccgacc cgtgaagacc gtatcggtat atgcaagggt     780
atcttcagaa ctgacaagat caaggacgaa gacattgtca gacttgttga tcagttccct     840
ggtcaatcta tcgatttctt cggtgctttg agggcgagag tgtacgatga tgaagtgagg     900
aagttcgttg agagccttgg agttgagaat atcggaaaga ggctggttaa ctcaagggaa     960 ggacccccg tgttcgagca acccgagatg acttatgaga gcttatggga atacggaaac    1020
atgcttgtga tggaacaaga gaatgtcaag agagtccaac ttgccgagac ctacctcagc    1080
caggctgctc tgggagacgc aaacgctgac gccatcggcc gcggaacttt ctacggtaaa    1140
acagaggaaa aggagcccag caagctcgag taa                                 1173
```

<210> SEQ ID NO 22
<211> LENGTH: 390
<212> TYPE: PRT
<213> ORGANISM: Artificial Sequence
<220> FEATURE:
<223> OTHER INFORMATION: Based on Arabidopsis thaliana sequence

<400> SEQUENCE: 22

| Met | Val | Lys | Glu | Asp | Lys | Gln | Thr | Asp | Gly | Asp | Arg | Trp | Arg | Gly | Leu |
|---|---|---|---|---|---|---|---|---|---|---|---|---|---|---|---|
| 1 | | | | 5 | | | | | 10 | | | | | 15 | |

| Ala | Tyr | Asp | Thr | Ser | Asp | Asp | Gln | Gln | Asp | Ile | Thr | Arg | Gly | Lys | Gly |
|---|---|---|---|---|---|---|---|---|---|---|---|---|---|---|---|
| | | | 20 | | | | | 25 | | | | | 30 | | |

| Met | Val | Asp | Ser | Val | Phe | Gln | Ala | Pro | Met | Gly | Thr | Gly | Thr | His | His |
|---|---|---|---|---|---|---|---|---|---|---|---|---|---|---|---|
| | | 35 | | | | | 40 | | | | | 45 | | | |

| Ala | Val | Leu | Ser | Ser | Tyr | Glu | Tyr | Val | Ser | Gln | Gly | Leu | Arg | Gln | Tyr |
|---|---|---|---|---|---|---|---|---|---|---|---|---|---|---|---|
| | 50 | | | | | 55 | | | | | 60 | | | | |

| Asn | Leu | Asp | Asn | Met | Met | Asp | Gly | Phe | Tyr | Ile | Ala | Pro | Ala | Phe | Met |
|---|---|---|---|---|---|---|---|---|---|---|---|---|---|---|---|
| 65 | | | | | 70 | | | | | 75 | | | | | 80 |

| Asp | Lys | Leu | Val | Val | His | Ile | Thr | Lys | Asn | Phe | Leu | Thr | Leu | Pro | Asn |
|---|---|---|---|---|---|---|---|---|---|---|---|---|---|---|---|
| | | | | 85 | | | | | 90 | | | | | 95 | |

| Ile | Lys | Val | Pro | Leu | Ile | Leu | Gly | Ile | Trp | Gly | Gly | Lys | Gly | Gln | Gly |
|---|---|---|---|---|---|---|---|---|---|---|---|---|---|---|---|
| | | | 100 | | | | | 105 | | | | | 110 | | |

| Lys | Ser | Phe | Gln | Cys | Glu | Leu | Val | Met | Ala | Lys | Met | Gly | Ile | Asn | Pro |
|---|---|---|---|---|---|---|---|---|---|---|---|---|---|---|---|
| | | 115 | | | | | 120 | | | | | 125 | | | |

| Ile | Met | Met | Ser | Ala | Gly | Glu | Leu | Glu | Ser | Gly | Asn | Ala | Gly | Glu | Pro |
|---|---|---|---|---|---|---|---|---|---|---|---|---|---|---|---|
| | 130 | | | | | 135 | | | | | 140 | | | | |

| Ala | Lys | Leu | Ile | Arg | Gln | Arg | Tyr | Arg | Glu | Ala | Ala | Asp | Leu | Ile | Lys |
|---|---|---|---|---|---|---|---|---|---|---|---|---|---|---|---|
| 145 | | | | | 150 | | | | | 155 | | | | | 160 |

| Lys | Gly | Lys | Met | Cys | Cys | Leu | Phe | Ile | Asn | Asp | Leu | Asp | Ala | Gly | Ala |
|---|---|---|---|---|---|---|---|---|---|---|---|---|---|---|---|
| | | | | 165 | | | | | 170 | | | | | 175 | |

| Gly | Arg | Met | Gly | Gly | Thr | Thr | Gln | Tyr | Thr | Val | Asn | Asn | Gln | Met | Val |
|---|---|---|---|---|---|---|---|---|---|---|---|---|---|---|---|
| | | | 180 | | | | | 185 | | | | | 190 | | |

| Asn | Ala | Thr | Leu | Met | Asn | Ile | Ala | Asp | Asn | Pro | Thr | Asn | Val | Gln | Leu |
|---|---|---|---|---|---|---|---|---|---|---|---|---|---|---|---|
| | | 195 | | | | | 200 | | | | | 205 | | | |

| Pro | Gly | Met | Tyr | Asn | Lys | Glu | Glu | Asn | Ala | Arg | Val | Pro | Ile | Ile | Cys |
|---|---|---|---|---|---|---|---|---|---|---|---|---|---|---|---|
| | 210 | | | | | 215 | | | | | 220 | | | | |

| Thr | Gly | Asn | Asp | Phe | Ser | Thr | Leu | Tyr | Ala | Pro | Leu | Ile | Arg | Asp | Gly |
|---|---|---|---|---|---|---|---|---|---|---|---|---|---|---|---|
| 225 | | | | | 230 | | | | | 235 | | | | | 240 |

| Arg | Met | Glu | Lys | Phe | Tyr | Trp | Ala | Pro | Thr | Arg | Glu | Asp | Arg | Ile | Gly |
|---|---|---|---|---|---|---|---|---|---|---|---|---|---|---|---|
| | | | | 245 | | | | | 250 | | | | | 255 | |

| Ile | Cys | Lys | Gly | Ile | Phe | Arg | Thr | Asp | Lys | Ile | Lys | Asp | Glu | Asp | Ile |
|---|---|---|---|---|---|---|---|---|---|---|---|---|---|---|---|
| | | | 260 | | | | | 265 | | | | | 270 | | |

| Val | Arg | Leu | Val | Asp | Gln | Phe | Pro | Gly | Gln | Ser | Ile | Asp | Phe | Phe | Gly |
|---|---|---|---|---|---|---|---|---|---|---|---|---|---|---|---|
| | | 275 | | | | | 280 | | | | | 285 | | | |

| Ala | Leu | Arg | Ala | Arg | Val | Tyr | Asp | Asp | Glu | Val | Arg | Lys | Phe | Val | Glu |
|---|---|---|---|---|---|---|---|---|---|---|---|---|---|---|---|
| | 290 | | | | | 295 | | | | | 300 | | | | |

| Ser | Leu | Gly | Val | Glu | Asn | Ile | Gly | Lys | Arg | Leu | Val | Asn | Ser | Arg | Glu |
|---|---|---|---|---|---|---|---|---|---|---|---|---|---|---|---|
| 305 | | | | | 310 | | | | | 315 | | | | | 320 |

| Gly | Pro | Pro | Val | Phe | Glu | Gln | Pro | Glu | Met | Thr | Tyr | Glu | Lys | Leu | Met |
|---|---|---|---|---|---|---|---|---|---|---|---|---|---|---|---|
| | | | | 325 | | | | | 330 | | | | | 335 | |

| Glu | Tyr | Gly | Asn | Met | Leu | Val | Met | Glu | Gln | Glu | Asn | Val | Lys | Arg | Val |
|---|---|---|---|---|---|---|---|---|---|---|---|---|---|---|---|
| | | | 340 | | | | | 345 | | | | | 350 | | |

| Gln | Leu | Ala | Glu | Thr | Tyr | Leu | Ser | Gln | Ala | Ala | Leu | Gly | Asp | Ala | Asn |
|---|---|---|---|---|---|---|---|---|---|---|---|---|---|---|---|
| | | 355 | | | | | 360 | | | | | 365 | | | |

```
Ala Asp Ala Ile Gly Arg Gly Thr Phe Tyr Gly Lys Thr Glu Glu Lys
    370                 375                 380

Glu Pro Ser Lys Leu Glu
385                 390

<210> SEQ ID NO 23
<211> LENGTH: 17
<212> TYPE: DNA
<213> ORGANISM: Artificial Sequence
<220> FEATURE:
<223> OTHER INFORMATION: primer

<400> SEQUENCE: 23
cagacaatgt tggcctc                                                 17

<210> SEQ ID NO 24
<211> LENGTH: 18
<212> TYPE: DNA
<213> ORGANISM: Artificial Sequence
<220> FEATURE:
<223> OTHER INFORMATION: primer

<400> SEQUENCE: 24
acgagtaacg atggtagg                                                18

<210> SEQ ID NO 25
<211> LENGTH: 15
<212> TYPE: DNA
<213> ORGANISM: Artificial Sequence
<220> FEATURE:
<223> OTHER INFORMATION: primer

<400> SEQUENCE: 25
gtctatacct tgagc                                                   15

<210> SEQ ID NO 26
<211> LENGTH: 14
<212> TYPE: DNA
<213> ORGANISM: Artificial Sequence
<220> FEATURE:
<223> OTHER INFORMATION: primer

<400> SEQUENCE: 26
tcagtcatac tcgg                                                    14
```